(12) United States Patent
Fein et al.

(10) Patent No.: US 9,180,132 B2
(45) Date of Patent: Nov. 10, 2015

(54) ANTIMICROBIAL CATIONIC STEROIDS AND METHODS OF USE

(75) Inventors: David E. Fein, Warrington, PA (US);
Robert Bucki, Philadelphia, PA (US);
Paul A. Janmey, Media, PA (US); Scott L. Diamond, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/581,988

(22) PCT Filed: Mar. 4, 2011

(86) PCT No.: PCT/US2011/027177
§ 371 (c)(1),
(2), (4) Date: Feb. 11, 2013

(87) PCT Pub. No.: WO2011/109704
PCT Pub. Date: Sep. 9, 2011

(65) Prior Publication Data
US 2013/0137668 A1 May 30, 2013

Related U.S. Application Data

(60) Provisional application No. 61/310,614, filed on Mar. 4, 2010.

(51) Int. Cl.
*A61K 31/56* (2006.01)
*A61K 31/57* (2006.01)
*A61K 31/573* (2006.01)

(52) U.S. Cl.
CPC .............. *A61K 31/57* (2013.01); *A61K 31/573* (2013.01)

(58) Field of Classification Search
None
See application file for complete search history.

(56) References Cited

U.S. PATENT DOCUMENTS 7,442,386 B2 * 10/2008 Diamond et al. ............. 424/450
2009/0124591 A1 * 5/2009 Diamond et al. ............. 514/183

FOREIGN PATENT DOCUMENTS

WO 9638464 A1 12/1996
WO 02077007 A2 10/2002

OTHER PUBLICATIONS

Helicobacter Pylori infections, Medline Plus, Nov. 26, 2014, http://www.nlm.nih.gov/medlineplus/helicobacterpyloriinfections.html.*
Behr et al., "Efficient gene transfer into mammalian primary endocrine cells with lipopolyamine-coated DNA." 1989, Proc Natl Acad Sci U S A., 86:6982-6986.
Blagbrough et al., "Polyamines and novel polyamine conjugates interact with DNA in ways that can be exploited in non-viral gene therapy." 2003, Biochem Soc Trans, 31:397-406.
Bucki and Janmey, "Interaction of the gelsolin-derived antibacterial PBP 10 peptide with lipid bilayers and cell membranes." 2006, Antimicrob Agents Chemother, 50:2932-2940.
Bucki et al., "Antibacterial Activities of Rhodamine B-Conjugated Gelsolin-Derived Peptides Compared to Those of the Antimicrobial Peptides Cathelicidin LL37, Magainin II, and Melittin" 2004, Antimicrob Agents Chemother 48:1526-1533.
Bucki et al., "Release of the antimicrobial peptide LL-37 from DNA/F-actin bundles in cystic fibrosis sputum." 2007, Eur Respir J 29:624-632.
Bucki et al., "Resistance of the antibacterial agent ceragenin CSA-13 to inactivation by DNA or F-actin and its activity in cystic fibrosis sputum." 2007, J Antimicrob Chemother, 60:535-545.
Caracciolo et al., "Transfection efficiency boost by designer multicomponent lipoplexes." 2007, Biochim Biophys Acta, 1768:2280-2292.
Chin et al., "Antimicrobial activities of ceragenins against clinical isolates of resistant Staphylococcus aureus." 2007, Antimicrob Agents Chemother 51:1268-1273.
Ding et al., "Correlation of the antibacterial activities of cationic peptide antibiotics and cationic steroid antibiotics." 2002, J Med Chem 45:663-9.
Fein et al., "Cationic lipid formulations alter the in vivo tropism of AAV2/9 vector in lung." 2009, Mol Ther 17(12):2078-87.
Gruneich et al., "Cationic corticosteroid for nonviral gene delivery." 2004, Gene Ther, 11:668-674.
Kichler et al., "Cationic steroid antibiotics demonstrate DNA delivery properties." 2005, J Control Release, 107:174-182.
Martin et al., "The design of cationic lipids for gene delivery." 2005, Curr Pharm Des, 11:375-394 (abstract).
Price et al., "Targeting viral-mediated transduction to the lung airway epithelium with the anti-inflammatory cationic lipid dexamethasone-spermine." 2005, Mol Ther, 12:502-509.
Price et al., "Pulmonary delivery of adenovirus vector formulated with dexamethasone-spermine facilitates homologous vector re-administration." 2007, Gene Ther, 14:1594-1604.
Salunke et al., "New steroidal dimers with antifungal and antiproliferative activity." 2004, J Med Chem, 47:1591-1594.
Wang and MacDonald, "New strategy for transfection: mixtures of medium-chain and long-chain cationic lipids synergistically enhance transfection." 2004, Gene Ther, 11:1358-1362.
Wang and MacDonald, "Synergistic effect between components of mixtures of cationic amphipaths in transfection of primary endothelial cells." 2007, Mol Pharm, 4:615-623.
Wang et al., "Transfection activity of binary mixtures of cationic o-substituted phosphatidylcholine derivatives: the hydrophobic core strongly modulates physical properties and DNA delivery efficacy." 2006, Biophys J, 91:3692-3706.
Bucki, et al., "Combined Antibacterial and Anti-Inflammatory Activity of a Cationic Disubstituted Dexamethasone Spermine Conjugate", Antimicrobial Agents and Chemotherapy 54(6), Jun. 1, 2010, 2525-2533.

(Continued)

*Primary Examiner* — Dennis Heyer
*Assistant Examiner* — Daniel M Podgorski
(74) *Attorney, Agent, or Firm* — Saul Ewing LLP; Kathryn Doyle; Domingos J. Silva

(57) ABSTRACT

The invention relates generally to antimicrobial cationic steroid pharmaceutical compositions, methods of making antimicrobial cationic steroid pharmaceutical compositions, and methods of using antimicrobial cationic steroid pharmaceutical compositions.

7 Claims, 25 Drawing Sheets

(56) References Cited

OTHER PUBLICATIONS

Fein, et al., "Cationic Lipid Formulations Alter the In Vivo Tropism of AAV2/9 Vector in Lung", Mol Ther. 17(12), Dec. 2009, 2078-2087.

Fein, et al., "Improved Gene Transfer to Lung Airway Epithelium with AAV Vectors Formulated with Steroidal Cationic Lipids", Molecular Therapy vol. 17, Supplement 1, May 2009, S124.

Fein, et al., "Novel Cationic Lipids with Enhanced Gene Delivery and Antimicrobial Activity", Molecular Pharmacology 78(3), Sep. 1, 2010, 402-410.

Savage, et al., "Antibacterial properties of cationic steroid antibiotics", FEMS Microbiology Letters 217(1), Nov. 1, 2002, 1-7.

* cited by examiner

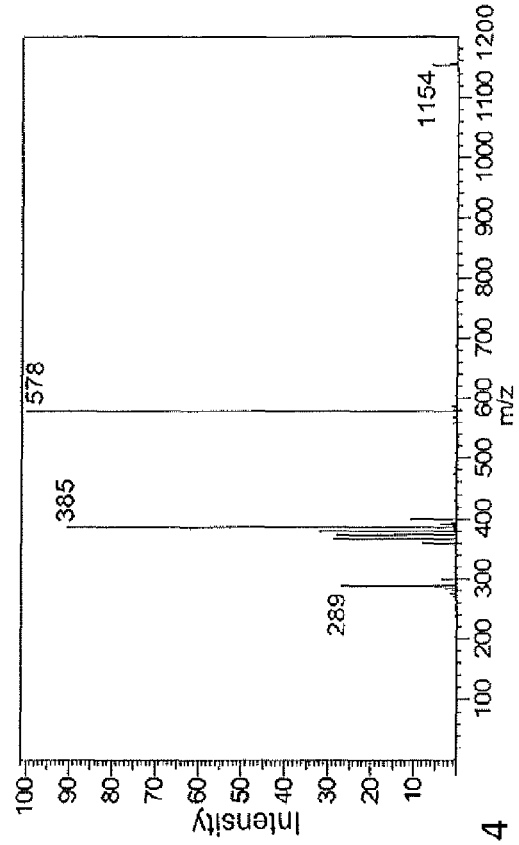
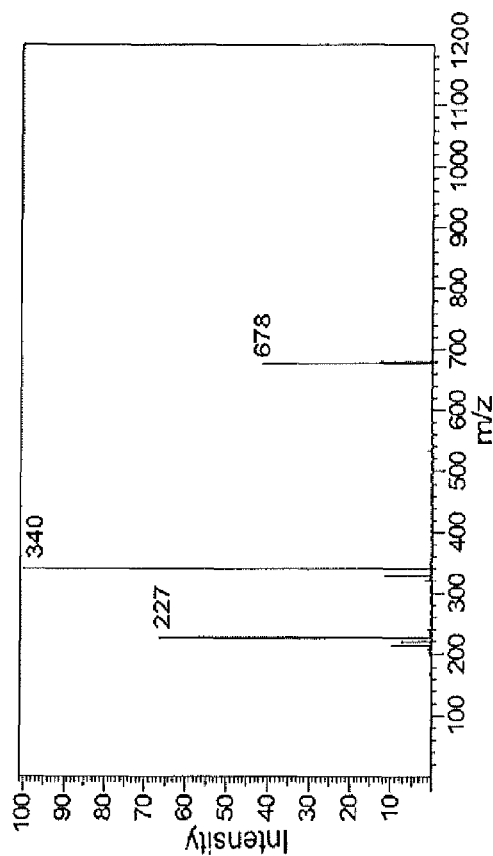
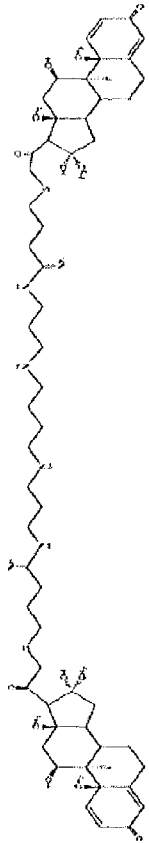
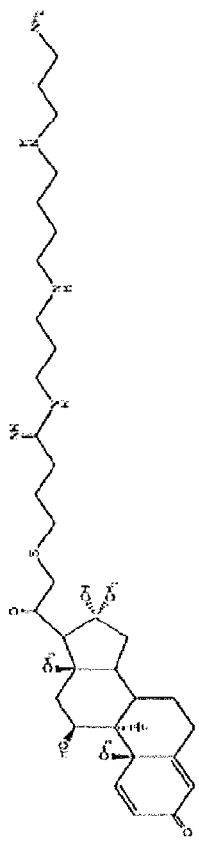
Figure 4

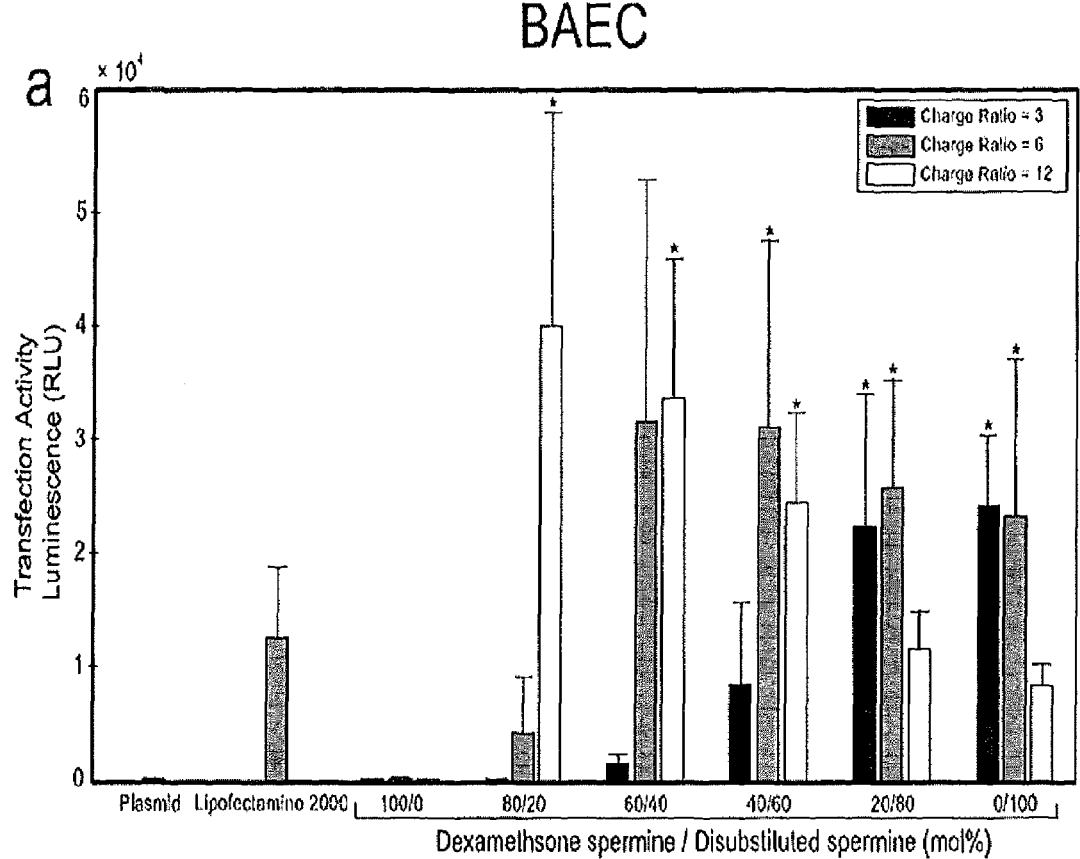
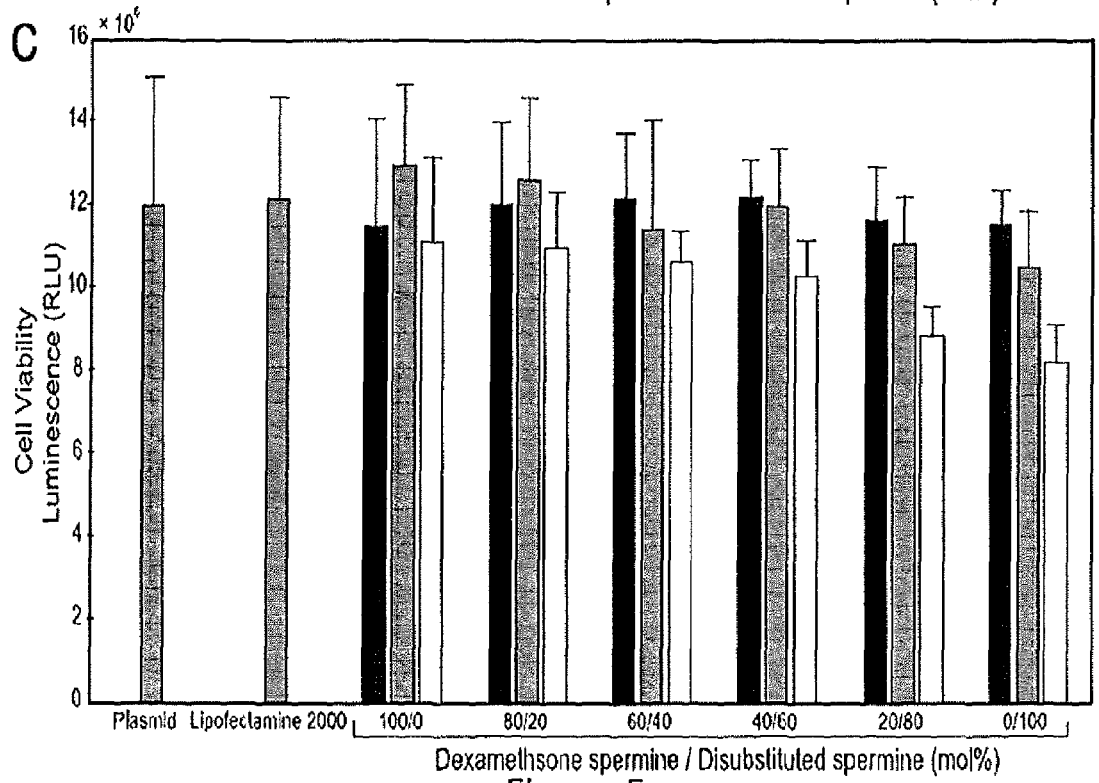
Figure 5

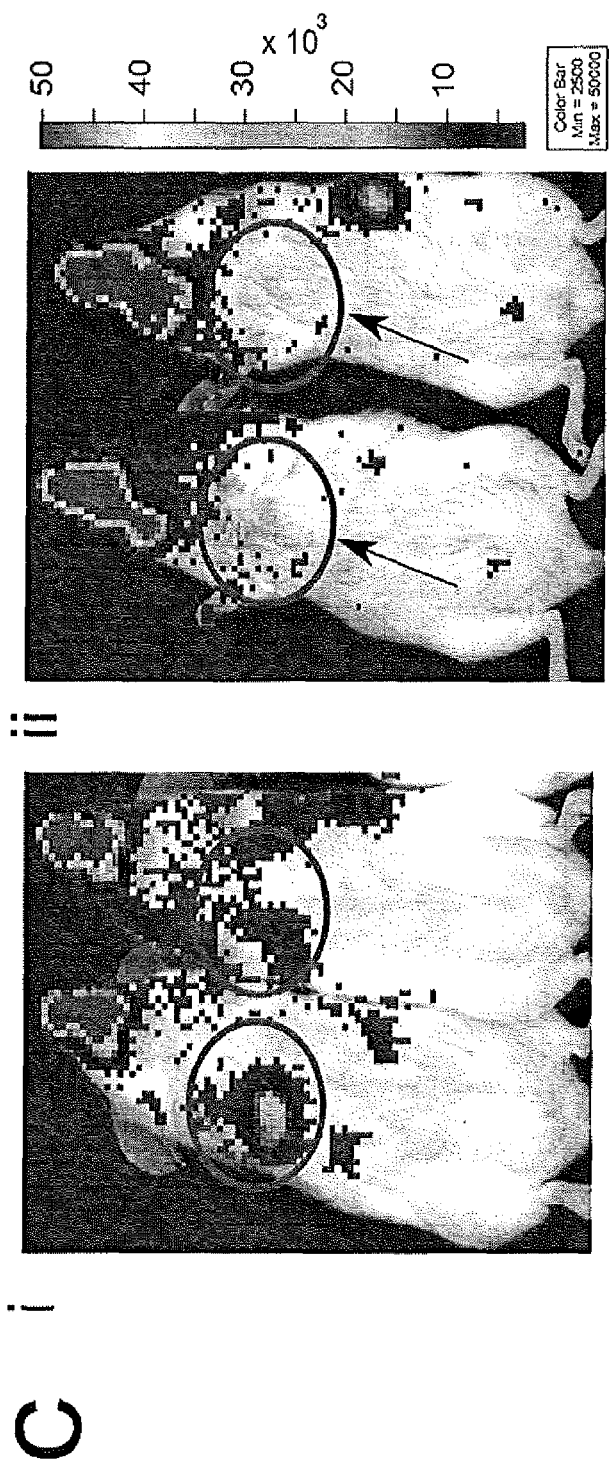
Figure 7cont'd

LL37:
LLGDFFRKSKEKIGKEFKRIVQRIKDFLRNLVPRTES

HB71:
FAKKLAKKLKKLAKKLAK

Disubstituted spermin (D2S):

| Bacteria strain | Antibacterial agents μg/ml) | | |
| --- | --- | --- | --- |
| | LL-37 (MBC/MIC) | D2S(MBC/MIC) | AMC (MIC) |
| Staphylococcus aureus ATCC 29213 | 6.3/3.125 | 1.6/1.6 | 1 |
| Streptococcus salivarius ATCC 13419 | 6.25/3.125 | 1.6/0.8 | 0.125 |
| Streptococcus sanquinis ATCC 10556 | 6.25/3.125 | 1.6/1.6 | 0.125 |
| Streptococcus mutans ATCC 35668 | 6.25/6.25 | 0.8/0.8 | 0.125 |
| Streptococccus pneumoniae* | 3.125/3.125 | 0.8/0.4 | 0.05 |
| Streptococcus pyogenes* | 3.125/3.125 | 1.6/0.8 | 0.025 |
| Enterococcus faecalis ATCC 29212 | 12.5/6.25 | 1.6/0.8 | 1 |
| Moraxella catarrhalis ATCC 23246 | 6.25/6.25 | 1.6/0.8 | 0.25 |
| Helicobacter pylori* | 6.25/3.125 | 0.8/0.4 | 0.025 |
| Peptostreptococcus anaerobius ATCC 27337 | 50/50 | 25/12.5 | 4 |
| Porphyromonas qinqivalis ATCC 33277 | 50/50 | 12.5/12.5 | 4 |
| Fusobacterium nucleatum ATCC 25586 | 50/50 | 25/12.5 | 8 |
| Lactobacillus casei ssp. casei ATCC 393 | 50/50 | 50/25 | 8 |
| Tannerella forsythensis ATCC 43037 | 50/50 | 25/12.5 | 8 |
| Pseudomonas aeruginosa Xen 5 (derived from P. aeruginosa strain ATCC 19660) | 100/50 | 6.25/6.25 | 8 |

Figure 16

| Bacteria (*clinical strain obtained from dental plaque) | Time | MBC/MIC (µg/ml) in presence of dental plaque suspended in saliva 1:10 (x=not determined) | |
|---|---|---|---|
| | | LL-37 | D2S |
| Staphylococcus aureus ATCC 29213 | 10' | 50/x | 12.5/x |
| | | 50/x | 6.25/x |
| | | 50/x | 6.25/x |
| | 30' | 12,5/x | 3.125/x |
| | | 25/x | 3.125/x |
| | | 25/x | 1,6/x |
| | 18h | 6.25/6.25 | 3.125/3.125 |
| | | 12.5/6.25 | 3.125/1.6 |
| | | 12.5/6.25 | 3.125/1.6 |
| Streptococcus salivarius* | 10' | 50/x | 12.5/x |
| | | 50/x | 6.25/x |
| | | 25/x | 6.25/x |
| | 30' | 12.5/x | 3.125/x |
| | | 25/x | 3.125/x |
| | | 12.5/x | 3.125/x |
| | 18h | 12.5/6.25 | 1.6/0.8 |
| | | 12.5/6.25 | 1.6/1.6 |
| | | 6.25/6.25 | 1.6/1.6 |
| Streptococcus mutant* | 10' | 25/x | 12.5/x |
| | | 50/x | 12.5/x |
| | | 50/x | 12.5/x |
| | 30' | 12,5/x | 3.125/x |
| | | 25/x | 1.6/x |
| | | 25/x | 1.6/x |
| | 18h | 6.25/6.25 | 1.6/0.8 |
| | | 12.5/6.25 | 1.6/1.6 |
| | | 12.5/6.25 | 1.6/1.6 |
| Enterococcus faecalis* | 10' | 75/x | 12.5/x |
| | | 100/x | 12.5/x |
| | | 75/x | 12.5/x |
| | 30' | 25/x | 3.125/x |
| | | 50/x | 3.125/x |
| | | 12,5/x | 3.125/x |
| | 18h | 25/6.25 | 1.6/1.6 |
| | | 25/6.25 | 1.6/0.8 |
| | | 12.5/6.25 | 1.6/0.8 |
| Helicobacter pylori* | 10' | 50/x | 12,5/x |
| | | 25/x | 6.25/x |
| | | 25/x | 6.25/x |
| | 30' | 25/x | 3.125/x |
| | | 12.5/x | 1.6/x |
| | | 12.5/x | 1.6/x |
| | 18h | 12.5/6.25 | 1.6/1.6 |
| | | 6.25/6.25 | 1.6/1.6 |
| | | 6.25/6.25 | 1.6/1.6 |

Figure 17

| Body fluid | Antibacterial agents (µg/ml) | |
|---|---|---|
| | LL-37 (MBC/MIC) | D2S (MBC/MIC) |
| Phosphate buffer | 204.8/>204.8 | 25.6/51.2 |
| Plasma | >204.8/>204.8 | 102.4/>204.8 |
| Cerebrospinal fluid | 102.4/>204.8 | 25.6/25.6 |
| Saliva | 204.8/>204.8 | 12.8/51.2 |
| Abdominal fluid | 204.8/>204.8 | 51.2/51.2 |
| BAL | 102.4/>204.8 | 25.6/51.2 |
| Urine | 102.4/204.8 | 51.2/102.4 |

Figure 18

| Body fluid | Antibacterial agents (µg/ml) | |
|---|---|---|
| | LL-37 (MBC/MIC) | D2S (MBC/MIC) |
| Phosphate buffer | 25.6/6.4 | 6.4/12.8 |
| Plasma | >204.8/>204.8 | 51.2/102.4 |
| Cerebrospinal fluid | 12.8/51.2 | 0.4/6.4 |
| Saliva | 12.8/51.2 | 1.6/12.8 |
| Abdominal fluid | 204.8/>204.8 | 12.8/51.2 |
| BAL | 12.8/12.8 | 25.6/51.2 |
| Urine | 51.2/204.8 | 12.8/12.8 |

Figure 19 ary Application No. 61/310,614, filed Mar. 4, 2010, each of
ANTIMICROBIAL CATIONIC STEROIDS AND METHODS OF USE

CROSS-REFERENCE TO RELATED APPLICATION

The present application is a 35 U.S.C. §371 national phase application from, and claiming priority to, International Application No. PCT/US2011/027177, filed Mar. 4, 2011, and published under PCT Article 21(2) in English, which is entitled to priority under 35 U.S.C. §119(e) to U.S. Provisional Application No. 61/310,614, filed Mar. 4, 2010, each of which applications are incorporated by reference herein in their entireties.

BACKGROUND OF THE INVENTION

Viral and non-viral vectors are used as the basis for gene delivery in current nucleic acid and gene therapy methods. However, there are concerns about the production, reproducibility, cost, and safety of viral vectors for gene therapy. As a result, work has focused on the development of nonviral vectors where the gene construct of interest is delivered by synthetic nonviral materials. Examples of such materials include polycations, dendrimers, and polysaccharides, as well as small molecule cationic lipids such as 3-beta-[N', N'dimethylaminoethane)-carbamoyl]cholesterol (DC-chol). Cationic lipids for lipofection condense plasmids, facilitate enclose escape, neutralize charge of DNA, and/or shield DNA from nucleases (basic, 1997, Liposomes in Gene Delivery, CRC Press).

Cationic lipids facilitate plasmid delivery and some cationic sterol-based compounds are known to possess antimicrobial activity due to their amphiphilic character. Given the persistent bacterial infection associated with several diseases targeted by gene therapy such as cystic fibrosis (Beadier, 2007, Annual Rev Med, 58:157-170) and the potential consequence of infections on the efficacy of gene delivery administration, antibacterial activity exhibited by the gene delivery vehicle would offer a therapeutic benefit.

Recently, several novel steroidal dimers have shown activity against certain pathogens and some compounds have been used to facilitate both in vitro transfection and bactericidal activity. (Blagbrough et al., 2003, Biochem Soc Trans, 31:397-406; Kichler et al., 2005, J Control Release, 107:174-182; Salunke et al., 2004, J Med Chem, 47:1591-1594). Facially amphiphilic lipid structures are believed to interact with membranes by an analogous mechanism to naturally incurring peptide antibiotics which are active against both gram-positive and gram-negative bacteria.

Cationic lipids are commonly used non-viral vectors for gene delivery duo to their ability to condense plasmid DNA (Hirko et al., Curr Med Chem, 10:1185-1193). Following synthesis of N-[1-(2,3-dioleyloxy)propyl]-N,N,N-trimethylammonium chloride (DOTMA) for lipofection (Felgner et al., 1987, PNAS, 84:7413-7417), optimization of the molecular structures of cationic lipids has been an active area of research including headgroup (Narang et al., 2005, Bioconjug Chem, 16:156-168; Obata et al., 2008, Bioconjug Chem, 19:1055-1063), linker (Bajaj et al., 2008, J Med Chem, 51: 2533-2540; Rajesh et al., 2007, J Am Chem See, 129:11408-11420; Aissaoui et al., 2004, J Med Chem, 47:5210-5223), and hydrophobic domain modifications (Remy et al., 1994, 5:647-654; Heyes et al., 2002, J Med Chem, 45; 99-114). Important modifications have included the use of multivalent polyamines, (Behr et al., 1989, PNAS, 86:6982-6986) which improve DNA binding and delivery via enhanced surface charge density (Martin et al., 2005, Curr Pharm Des, 11:375-394) and the use of sterol-based hydrophobic groups such as 3B—[N—(N,N-dimethylaminoethane)-carbamoyl]cholesterol (DC-Chol), which limits toxicity (Gao and Huang, 1991, Biochem Biophys Res Commun, 179:280-285). Helper lipids such as dioleoyl phosphatidylethanolamine (DOPE) are used to improve transgene expression via enhanced liposomal hydrophobicity and hexagonal inverted phase transition to facilitate endosomal escape (Karanth et al., 2007, J Pharm Pharmacol, 59:469-483). Studies of mixed lipids are less common; however, recent studies involving mixtures of cationic lipid derivatives have shown promise and represent an interesting new area for optimization (Wang and MacDonald, 2004, Gene Ther, 11:1358-1362; Wang and MacDonald, 2007, Mol Pharm, 4:615-623; Caracciolo et al., 2007, Biochim Biophys Acta, 1768:2280-2292). In addition to the molecular structures of cationic lipids, transfection efficiency has been linked to physicochemical characteristics and morphology of structures formed following complex formation with DNA (Ma et al., 2007, J Control Release, 123:184-194). Critical factors influencing transfection activity include lipoplex charge ratio (lipid:DNA), solution ionic strength, and residual net surface charge of lipoplexes (liposome-DNA complex).

Interestingly, several findings have indicated that inflammatory cytokines can inhibit gene transfer in vitro with a decrease in both transcription and transgene activity of ~50%. (Baatz et al., 2001, Biochim Biophys Acta, 1535:100-109; Bastonero et al., 2005, J Gene Med, 7:1439-1449). This inhibitory effect was prevented by glucocorticoid treatment indicating blocking the NF-KB pathway, which is known to control upregulation of numerous inflammatory cytokines including IL-8 and TNF-alpha (Kulms and Schwarz, 2006, Vitam Horm, 74:283-300), may play a critical role between induced inflammation and efficiency of gene transfer. In addition to the pathogenesis associated with infection, bacterial membrane bound molecules, such as lipopolysaccharide (LPS), are known to activate a strong inflammatory response in eukaryotic cells via toll-like receptors (TRL), especially TRL4, (Schnare et al., 2006, Int Arch Allergy Immunol, 139: 75-85) therefore, prevention of bacterial-mediated inflammation may also have a direct impact on gene delivery efficiency.

The activities of two sterol-based cationic lipids: dexamethasone-spermine (DS), (Gruneich et al., 2004, Gene Ther, 11:668-674) and disubstituted spermine ($D_2S$), resulting from conjugation of dexamethasone to the polyamine spermine DS, has been shown to exhibit anti-inflammatory activity in an in vivo mouse intraperitoneal thioglycollate challenge model based on neutrophil infiltration and has been shown to condense and deliver plasmid DNA enabling in vitro transfection of plasmid DNA. DS has also been shown to improve airway targeting, attenuate vector-induced inflammation, and facilitate re-administration in vivo when formulated with adenovirus vectors, (Price et al., 2005, Mol Ther, 12:502-509; Price et al., 2007, Gene Ther, 14:1594-1604; see also U.S. patent application Ser. No. 12/259,097).

There is a long felt need in the art for new antimicrobial compositions and methods of treatment. The present invention satisfies this need.

SUMMARY OF THE INVENTION

The invention provides a method of treating an infection in a subject. In one embodiment, the method comprises the steps of administering to a subject in need thereof, an antimicrobial cationic steroid pharmaceutical composition comprising a steroid-polyamine molecule, wherein the polyamine constituent of the steroid-polyamine molecule is attached through the C-21 position of the steroid constituent of the steroid-polyamine molecule. Preferably, the subject is a human.

In one embodiment, the infection is an oral infection.

In one, the cationic steroid pharmaceutical composition comprises an amphiphilic dimer, disubstituted polyamine, resulting from conjugation of two steroid constituents to both primary amines on the polyamine. Preferably, the polyamine is spermine. Preferably, the steroid is dexamethasone.

The invention provides a method of treating an infection in a subject comprising the steps of administering to a subject in need thereof, a antimicrobial cationic steroid pharmaceutical composition comprising a dexamethasone-spermine molecule, wherein the spermine constituent of said dexamethasone-spermine molecule is attached through the C-21 position of the dexamethasone constituent of the dexamethasone-spermine molecule. Preferably, the subject is a human.

In one embodiment, the infection is an oral infection.

In one embodiment, the antimicrobial cationic steroid pharmaceutical comprises an amphiphilic (Timer, disubstituted spermine, resulting from conjugation of two dexamethasone constituents to both primary amines on the spermine. Preferably, the polyamine is spermine. Preferably, the steroid is dexamethasone.

The invention also provides a method of treating an infection in a subject comprising the steps of administering to a subject in need thereof, an antimicrobial cationic steroid pharmaceutical composition made by a method comprising, mixing together a steroid, a conjugating reagent, and a polyamine, wherein the conjugating reagent conjugates the polyamine through the C-21 position of the steroid, purifying the conjugated steroid-polyamine molecule, thereby producing a cationic steroid pharmaceutical composition; and wherein the cationic steroid pharmaceutical composition treats the disease or disorder, thereby treating a disease or disorder in a subject. Preferably, the subject is a human.

In one embodiment, the infection is an oral infection.

In one embodiment, the antimicrobial cationic steroid pharmaceutical composition is an amphiphilic dimer, disubstituted polyamine, resulting from conjugation of two steroid constituents to both primary amines on the polyamine. Preferably, the polyamine is spermine. Preferably, the steroid is dexamethasone.

In one embodiment, the conjugating reagent is 2-iminothiolane.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings. In the drawings:

FIG. 4 depicts the results of an analysis of the structure of DS (1) and $D_2S$ (2) with mass spectrometry data showing multiple ionizations. Synthesis and purification of DS and $D_2S$ were adapted from the method described previously. (Gruneich et al., 2004, Gene Ther, 11:668-674; see also U.S. patent application Ser. No. 12/259,097) Single quadrupole mass spectrometry was performed using a Shimadzu (Columbia, Md.) LCMS coupled to a Hamilton (Reno, Nev.) PRP-1 column (150 mm×10 mm i.d., 10 µm particle size for semi-preparative separation or 150 mm×2.1 mm i.d., 5 µm particle size for analytical separation) using electrospray ionization (ESI) in positive ion mode with a scanned m/z range from 160-2000. The LCMS system consisted of a Shimadzu LC-20AB solvent delivery system coupled to a Shimadzu SPD20A dual wavelength UV-Vis detector and Shimadzu LCMS 2010EV mass spectrometer. $^1H$ and $^{13}C$ NMR analysis were performed with a Bruker AVANCE III 500 MHz instrument using a dual 5 min cryoprobe or a Bruker DMX 600 using a 5 mm TXI 3 axis grad probe.

FIGS. 5a through 5d, depicts the results of an example experiment evaluating the transfection of bovine aortic endothelial cells, BAECs (FIG. 5a) and A549 cells (FIG. 5b) using DS and $D_2S$ at three charge ratios with renilla luciferase transgene 24 hours after exposure to lipoplexes. Cell viability for BAECs (FIG. 5c) and A549 cells (FIG. 5d) following transfection was also assessed.

FIGS. 6a through 6c, depicts the results of an example experiment assessing the concentration kill curves for *E. Coli* MG1655 with mixtures of DS and $D_2S$ (FIG. 6a), and for *B. subtilis*, *P. aeruginosa* PA01, and *P. aeruginosa* PA01 in the presence of purified LPS (FIG. 6b). Red blood cell lysis in response to treatment with DS and $D_2S$ was also assessed (FIG. 6c).

FIGS. 7a through 7c, depicts the results of an example experiment assessing IL-8 release from neutrophils. $D_2S$ significantly prevented release of IL-8 from neutrophils in the presence of LPS (FIG. 7a).

FIGS. 8a through 8c, depicts the results of an experiment assessing the average effective diameter of mixtures of DS and $D_2S$ in water (FIG. 8a) and Optimem (FIG. 8b) from dynamic light scattering.

FIGS. 9A through 9H, depicts the results of an example experiment assessing the transfection of BAECs with DS and $D_2S$ using GFP transgene at a charge ratio of 6:1 at 24 hours.

Group A, B, C, and D represent data from 4 strains with similar characteristics; A—MRSA MLSB(±)/P-lactamase (+), B—MSSA MLSB(±)/P-lactamase (+), C—MSSA MLSB(−)/P-lactamase (+), D—MSSA MLSB(−)/P-lactamase (−). Error bars represent standard deviations from four measurements. Panel B. *P. aeruginosa* outgrowth from cystic fibrosis sputum samples after 1H treatment with D2S (0), LL-37 (*) and HB-71(0) peptides. Error bars represent standard deviations from eight measurements.

Figure 12:
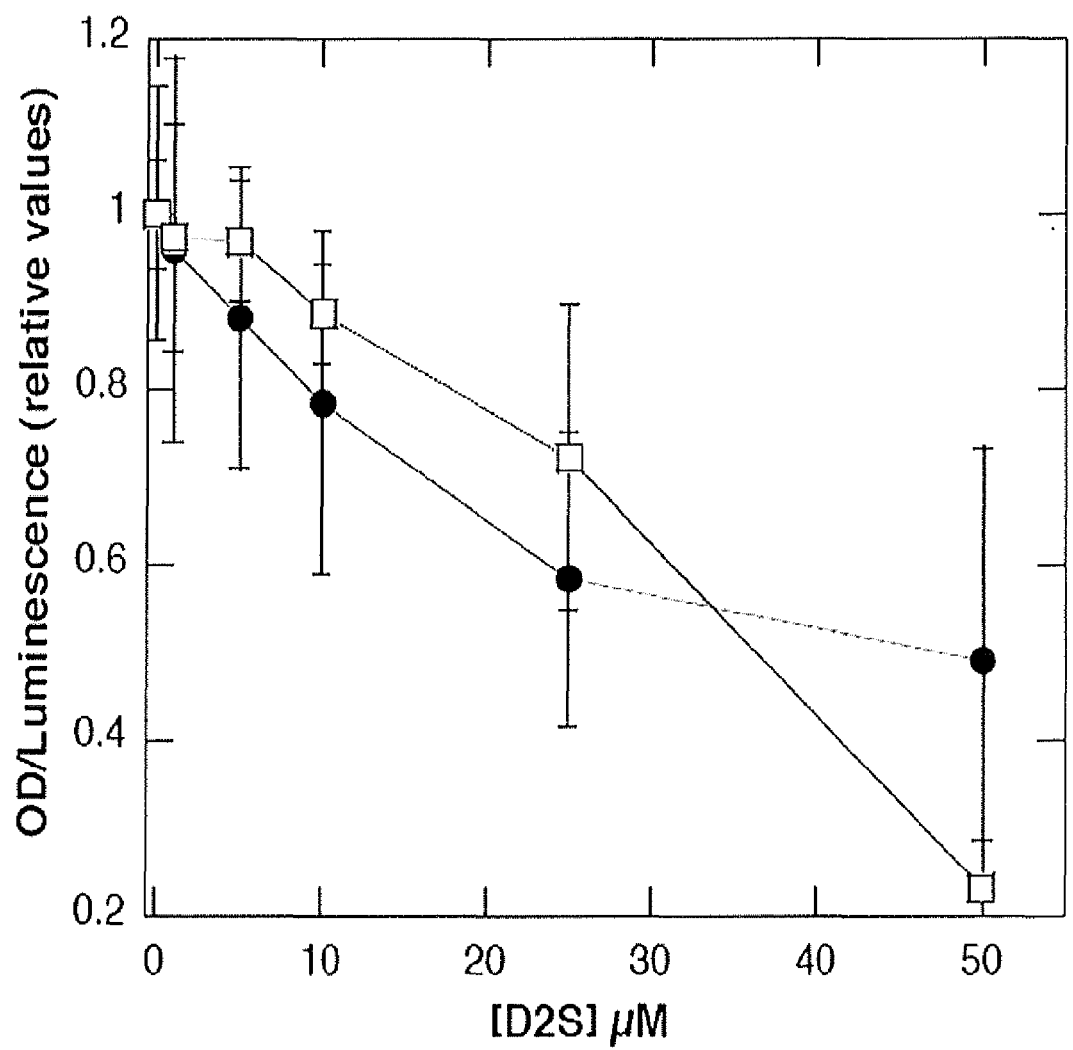

FIG. 12 depicts the results of an example experiment demonstrating the antibacterial activity of $D_2S$ against biofilm of mucoid strain of *P. aeruginosa* Xen 5, evaluated four hours after $D_2S$ administration. Slopes represent relative value of crystal violet absorbance (*) and Luminescence (0) that progressively decrease with addition of $D_2S$. Error bars represent standard deviations from three to five measurements.

Figure 13:
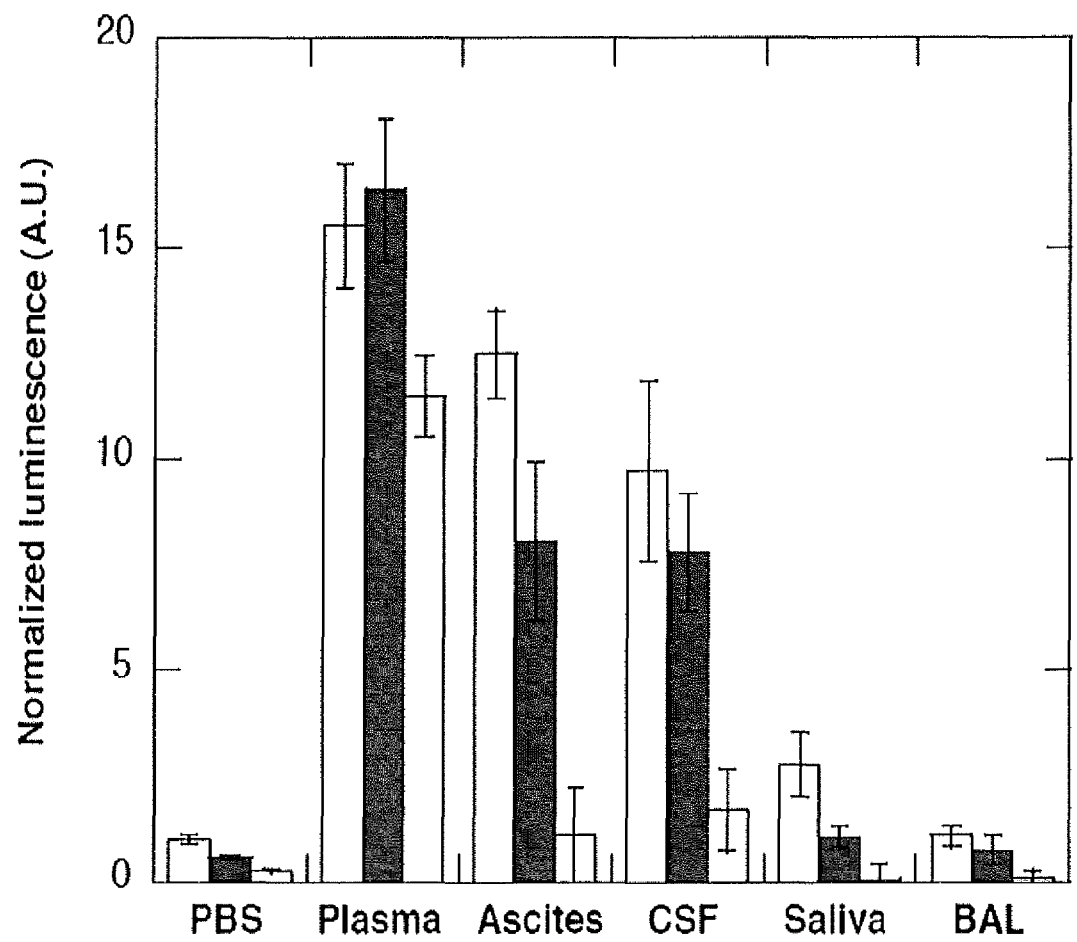

FIG. 13 depicts the results of an example experiment demonstrating the antibacterial activity of $D_2S$ against *P. aeruginosa* Xen 5 in different body fluids was determined based on luminescence reading 3 h after addition of equal amount of bacteria to equal volume of phosphate buffer saline (PBS), or PBS supplemented with 50% of human plasma, ascites, cerebra-spinal fluid (CSF), saliva, or bronchoalveolar lavage (BAL). In each condition, the white column indicates luminescent signal in control samples. Black and gray columns indicate luminescent signal in presence of 10 and 30 μM D2S respectively. Data from one experiment performed in triplicate are shown. Two other experiments with samples obtained from different subjects show similar trends.

Figure 14:
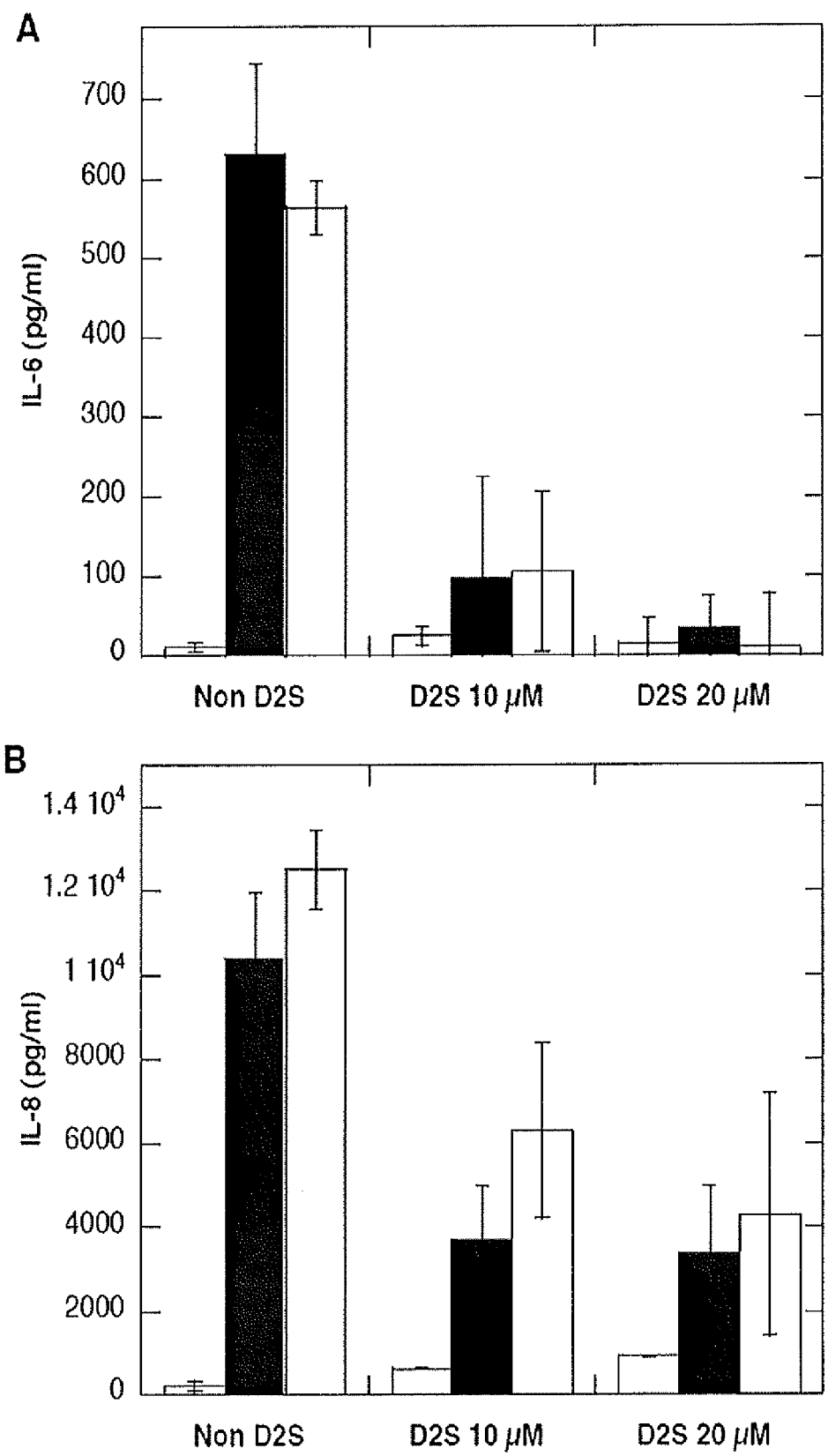

FIG. 14 depicts the results of an example experiment demonstrating that $D_2S$ inhibits IL-6 (panel A) and IL-8 (panel B) release from neutrophils treated with LPS (0.05 μg/ml) from *E. coli* (black column) or purified LTA (10 μg/ml) from *S. aureus* (gray column). White columns represent values obtained in control (non treated samples or neutrophils treated with indicated $D_2S$ amount). Error bars represent standard deviations from three measurements performed in duplicate. *Significantly different from neutrophil samples treated with LPS or LTA.

Figure 15:
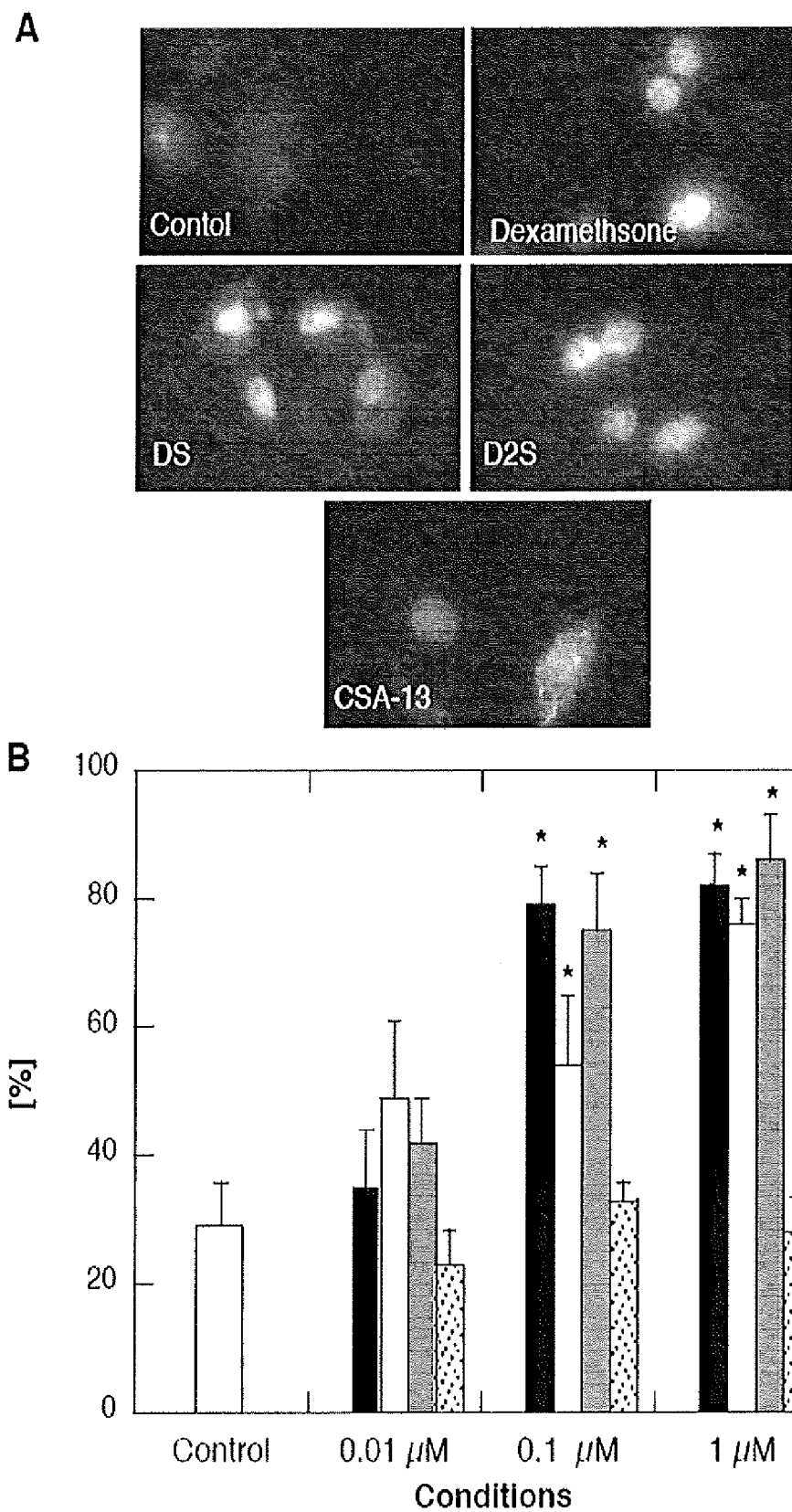

FIG. 15 depicts the results of an example experiment demonstrating $D_2S$-induced GFP-GR translocation from cytosol to nucleoplasm in BAECs. In this experiment BAECs were transfected with GFP-GR plasmid using lipofectamine as a gene delivery strategy. After transfection, cells were grown for 24 hours and activated with dexamethasone (black column), dexamethasone-spermine (light gray column), disubstituted-spermine (dark gray column), and ceragenin CSA-13 (speckled column), GFP-GR nucleus localization was evaluated with fluorescent microscope observation. *Significantly different from control sample.

FIG. 16 depicts the results of an example experiment demonstrating antibacterial activity of LL-37 peptide and D2S against pathogens associated with oral infections. *=clinical strain, AMC=amoxicillin/clavulonic acid 2:1.

FIG. 17 depicts the results of an example experiment demonstrating MBC/MIC values of LL-37 and D2S against bacterial isolated from dental plaque ($10^5$ CFU/ml) in suspension containing a mix of saliva with dental plaque (n=3).

FIG. 18 depicts the results of an example experiment demonstrating antibacterial activity of LL-37 peptide and D2S against *P. aeruginosa* Xen5 (~$10^8$ CFU/ml) in different body fluids (50%).

FIG. 19 depicts the results of an example experiment demonstrating antibacterial activity of LL-37 peptide and D2S against *S. aureus* Xen29 (~$10^8$ CFU/ml) in different body fluids (50%).

DETAILED DESCRIPTION

General Description

The invention relates generally to antimicrobial cationic steroid compositions, methods of making antimicrobial cationic steroid compositions, and methods of using antimicrobial cationic steroid compositions. The invention further relates to antimicrobial cationic steroid pharmaceutical compositions and methods for using cationic steroids for diminishing the number of microbes inhabiting an infected site of a subject.

The invention relates specifically to antimicrobial cationic steroid pharmaceutical compositions comprising a cationic steroid conjugated to a polyamine. In various embodiments, the antimicrobial cationic steroid composition is used in conjunction with a lipid. The methods of the invention include making the antimicrobial cationic steroid composition and methods of treating a subject in need thereof, by using the antimicrobial cationic steroid compositions of the invention to diminish the number of microbes on a treatment site of the subject. In some embodiments, the compositions and methods of the invention are also used for delivering molecules, such as nucleic acids, to cells or tissues, both in vivo and in vitro.

In various embodiments, the invention includes therapeutic, as well as non-therapeutic (antiseptic, germicidal, or disinfecting), treatment applications in which the compositions are placed in contact with an infected site to be treated, such as, for example, intact or broken skin. In some embodiments, the compositions and methods of the invention can be used for in vitro treatments, for example by adding the compound to a bacterial culture to test for susceptibility of a particular bacteria to a particular compound of the invention. In other embodiments, the compositions and methods of the invention can be used for in vivo treatments, for example by administering the compound to an infected site of a subject. Non-limiting examples of microbes that can be treated with the compositions and methods of the invention include bacteria such as *E. coli, B. subtilis, P. aeruginosa, E. cloacae, S. typhimurium, M. tuberculosis* and *S. aureus*. It should be noted that the compounds of the invention can be used to inhibit antibiotic-resistant strains of bacteria.

In some embodiments, the methods of treating an infected site of a subject further includes the combined administration of antibiotics. The appropriate antibiotic administered will typically depend on the susceptibility of the bacteria such as whether the bacteria is Gram-negative or Gram-positive, and will be easily discernable by one of skill in the art. Examples of particular antibiotics that can be used in combination in various embodiments of the invention include aminoglycosides tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). Further to the antibiotics listed above, typical antibiotics include aminoglycosides (amikacin, gentamicin, kanamycin, netilmicin, tobramycin, streptomycin, azithromycin, clarithromycin, erythromycin, erythromycin estolate/ethylsuccinate, gluceptate/lactobionate/stearate, beta-lactams such as penicillins (e.g., penicillin G, penicillin V, methicillin, nafcillin, oxacillin, cloxacillin, dicloxacillin, ampicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin, and polymyxins, such as PMB.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "alleviating a disease or disorder symptom," means reducing the severity of the symptom.

A "cationic steroid" is a sterol-based molecule that has a positive charge, or is part of a complex that has a positive charge, such as a steroid coupled with a polyamine.

The term "delivery vehicle," as used herein, refers to a molecule or composition useful for binding or carrying another molecule, such as a nucleic acid or drug, and delivering it to a target site, such as a cell. "Delivery vehicle" is used interchangeably with terms such as "drag delivery vehicle" "nucleic acid delivery vehicle," or "delivery vector."

The terms "patient," "subject" and "individual" are interchangeably used to mean a warm-blooded animal, such as a mammal, suffering from a disease, such as, but not limited to, a bacterial infection. It is understood that humans and animals are included within the scope of the term "patient," "subject" or "individual."

As used herein, the term "infection" is used to mean an area, a region or a site on the surface of, or inside the body of, a subject that exhibits signs or symptoms of infection, or colonization, by a microbe. The infected areas, regions and sites that can be treated with the compositions and methods of the invention include any area, region or site on the surface of, or inside the body of, a subject. By way of nonlimiting examples, infected areas, regions and sites that can be treated with the compositions and methods of the invention include, but are not limited to, external tissues (e.g. skin, etc.), internal tissues (e.g. mucosa, muscle, fascia, blood, etc.), and internal organs (e.g. lungs, liver, etc.). Moreover, "infection" should not be construed to include only those areas, regions or sites that exhibit overt evidence of infection, but rather should also be construed to include areas, regions or sites that may be colonized, subclinically infected and/or asymptomatic, i.e., that do not contain overt evidence of infection, but that may be affected nonetheless and that could, in time, exhibit more overt evidence of infection. By way of nonlimiting examples, such a site can include a trauma wound, surgical wound, intact tissue or burn that has come into contact with, or which is at risk of potentially coming into contact with, a pathogen that can colonize or infect the wound, and can be treated, or prophylactically treated, with the compositions and methods of the invention.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment," as applied to a nucleic acid, can ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g. as a cDNA or a genomic or cDNA fragment produced by PCR or restriction enzyme digestion) independent of other sequences. It also includes a recombinant DNA which is part of a hybrid gene encoding additional polypeptide sequence.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "peptide" typically refers to short polypeptides.

As used herein, the term "pharmaceutically-acceptable carrier" means a chemical composition with which an appropriate delivery vehicle and nucleic acid, drug, or compound can be combined and which, following the combination, can be used to administer the appropriate delivery vehicle and nucleic acid, drug, or compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Polyamine" as used herein refers to polymers of amines as well as to other types of molecules containing amines, such as amine rich polymers or other amine containing polymers, a lysine containing peptide, and an arginine containing peptide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

A "polynucleotide" means a single strand or parallel and anti-parallel strands of a nucleic acid. Thus, a polynucleotide may be either a single-stranded or a double-stranded nucleic acid.

A "prophylactic" treatment is a treatment administered to a subject who does not exhibit signs of a disease or exhibits only early signs of the disease for the purpose of decreasing the risk of developing pathology associated with the disease.

The term "protein" typically refers to large polypeptides.

"Slow release," as used herein, refers to delivery of a nucleic acid, drug, or molecule to a cell, tissue, or organ, wherein the nucleic acid, drug, or molecule is not all readily available because some remains bound to the delivery vehicle or to an anionic molecule and is slowly released for availability over a period of time. The period of time should be at least 10% longer than availability that is not slow release, preferably at least 25% longer, more preferably at least 35% longer, and even more preferably at least 50% longer. Such a drug or molecule can include a prodrug or steroid prodrug.

"Synthetic peptides or polypeptides" mean a non-naturally occurring peptide or polypeptide. Synthetic peptides or polypeptides can be synthesized, for example, using an automated polypeptide synthesizer. Those of skill in the art know of various solid phase peptide synthesis methods.

A "therapeutic" treatment is a treatment administered to a subject who exhibits signs of pathology, for the purpose of diminishing or eliminating those signs.

"Tissue," as used herein, refers to the general definition of tissue which includes a collection of similar cells and the intercellular substances and spaces surrounding them, and the term is also used herein to include collections of similar cells in tissues and organs.

The term "topical application," as used herein, refers to administration to a surface, such as the skin. This term is used interchangeably with "cutaneous application."

By "transdermal" delivery is intended both transdermal (or "percutaneous") and transmucosal administration, i.e., delivery by passage of a drug through the skin or mucosal tissue and into the bloodstream. Transdermal also refers to the skin as a portal for the administration of drugs or compounds by topical application of the drug or compound thereto.

The term "treat" or "treatment," as used herein, refers to the alleviation (i.e., "diminution") and/or the elimination of a symptom or a source of a symptom or of a given disease. By way of several non-limiting examples, a symptom of a bacterial infection can be treated by alleviating a symptom of that disorder. A symptom of a bacterial infection can also be treated by altogether eliminating a symptom of that disorder. A bacterial infection or colonization can be treated by alleviating the source, or "cause," of that disorder. A bacterial infection or colonization can also be treated by eliminating the source of that disorder.

A "vector," as used herein, refers to either a delivery vehicle as described herein or to a vector such as an expression vector.

DESCRIPTION

Synthesis and Hydrolysis of Cationic Steroids or Drugs for Use as Nucleic Acid and Drug Delivery Vehicles It has been discovered in the present invention that using novel methods steroids can be conjugated with a polyamine, and that the resultant molecule has antimicrobial activity (See Example 4). The invention further encompasses methods for making antimicrobial cationic steroid compositions. Furthermore, it is an aspect of the present invention that when coupled with a lipid, this antimicrobial cationic steroid composition is capable of delivering nucleic acids to cells (see Examples 1-3). It is a further aspect of the present invention that the antimicrobial cationic steroid compositions maintain its inherent biological activity once coupled with a polyamine.

The invention should be construed to include various steroids or hydrophobic drugs as described herein, including glucocorticoids, and should not be construed to include only the steroids described herein. Such steroids included, but are not limited to, a mineral corticoid, an androgen, an estrogen, a progestagen, an analog with steroidal agonist activity, an analog with steroidal antagonist activity, an inactive structural analog, and modifications or derivatives thereof. For example, additional steroids which are useful in the invention include, cortexolone mesylate, cortisone mesylate, prednisone 21-mesylate, 30-iodocholesterol, 16β-bromo-4-androsten-3,17-dione, 2α-bromo-5α-cholestan-3-one, 16α-bromoestradiol, 16α-bromoestrone, 16β-bromoestrone, 17α-bromopregnenolone, 17-bromoprogesterone, androsterone tosylate, cholestanol tosylate, cholesteryl tosylate, dehydroepiandrosterone tosylate, dihydrotestosterone tosylate, epiandrosterone tosylate, 11α-hydroxyprogesterone tosylate, 19-nortestosterone tosylate, pregnenolone tosylate, and testosterone tosylate. The invention should be construed to include active and inactive analogs, modifications, and derivatives of the steroids and drugs, as well as steroid prodrugs and prodrugs.

In addition, the invention should be construed to include various polyamines, including spermine. In addition to the polyamine spermine, the invention should be construed to include any other polyamine, including, but not limited to, spermidine, polylysine, proteins, peptides, oligonucleotides, other biopolymers, synthetic polyamines, such as polyamines (for example, polyethyleneimine), a lysine containing peptide, an arginine containing peptide, a cationic polymer, and an amine rich polymer, and amino dendrimers.

In one aspect of the invention the lipid is a cationic lipid and in another aspect the lipid contains both a cationic lipid and a neutral lipid. Neutral lipids of the invention include, but are not limited to, DOPE, phosphatidylcholine (PC), and cholesterol. Cationic lipids of the invention include, but are not limited to, dexamethasone spermine, disubstituted spermine, 3-beta-[N',N'dimethylaminoethane)-carbamoyl]cholesterol) (DC-Chol), N[1-(2,3-dioleyloxy)propyl[N,N,N-triethyl-ammonium (DOTMA), 2'-(1",2"-dioleoyloxypropyldimethylammonium bromide)-N-ethyl-6-aminospermine tetra trifluoroacetic acid (DOSPA), 1,3-bis(oleoyloxy)-3-(trimethylammonio)propane (DOTAP), and GL-67. In one aspect of the invention, the lipid contains a helper lipid to aid in delivery of a nucleic acid, drug, or other compound. Furthermore, the invention should be construed to include lipids other than those described herein.

In one embodiment of the invention a steroid and a polyamine such as spermine are coupled using a coupling reagent. In one aspect of the invention the reagent is 2-iminothiolane. In another aspect of the invention, a steroid or drug and spermine are also mixed with dimethylsulfoxide. In yet another aspect of the invention, a purified steroid-polyamine complex or purified drug-polyamine complex are mixed with a lipid to form a delivery vehicle which is also an antimicrobial cationic steroid composition.

Figure 1A:
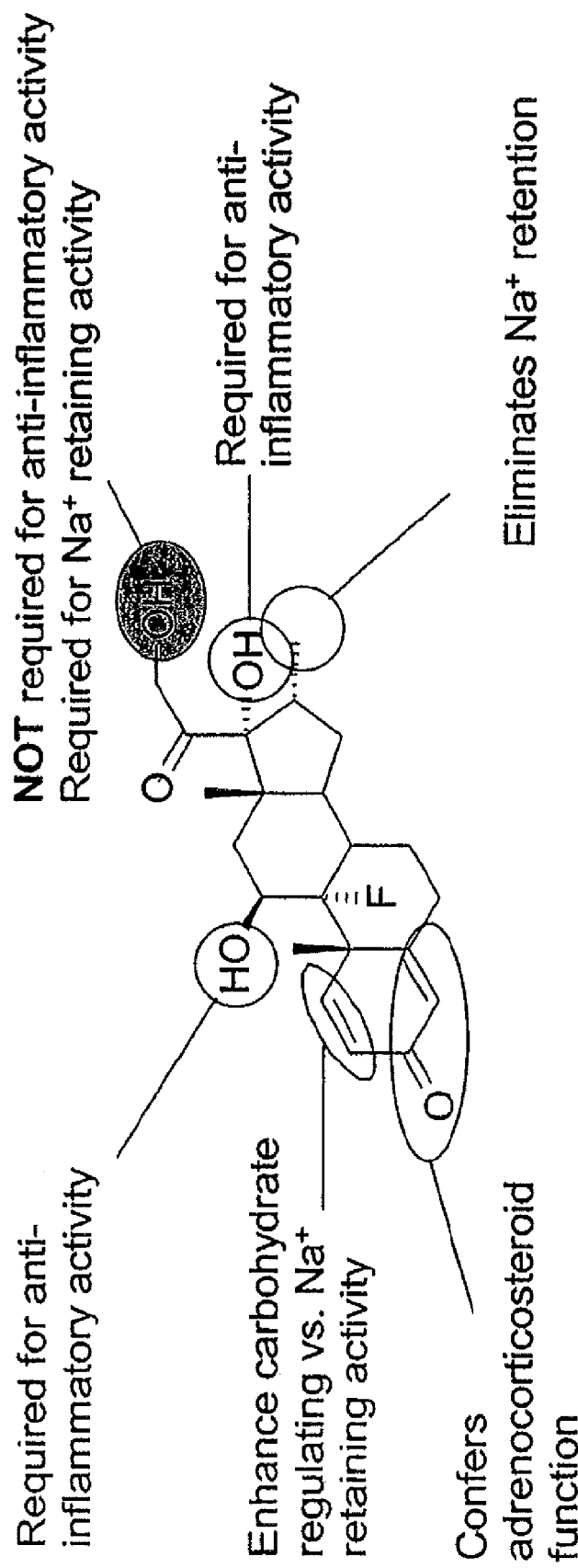
FIG. 1, comprising FIGS. 1A and 1B, schematically illustrates synthesis of a cationic steroid for nucleic acid or drug delivery and anti-inflammatory activity. The 21-hydroxy position of dexamethasone was chosen for conjugation of a cationic group (FIG. 1A).
In FIG. 1B it can be seen that the use of 2-iminothiolane (Traut's reagent) as a coupling reagent does not consume a cation on spermine during the synthesis of the cationic steroid, dexamethasone-spermine (DS; Product 1). Under basic conditions, the prodrug DS undergoes hydrolysis, releasing spermine and a dexamethasone-amide (DA; Product 2).
Figure 1B:
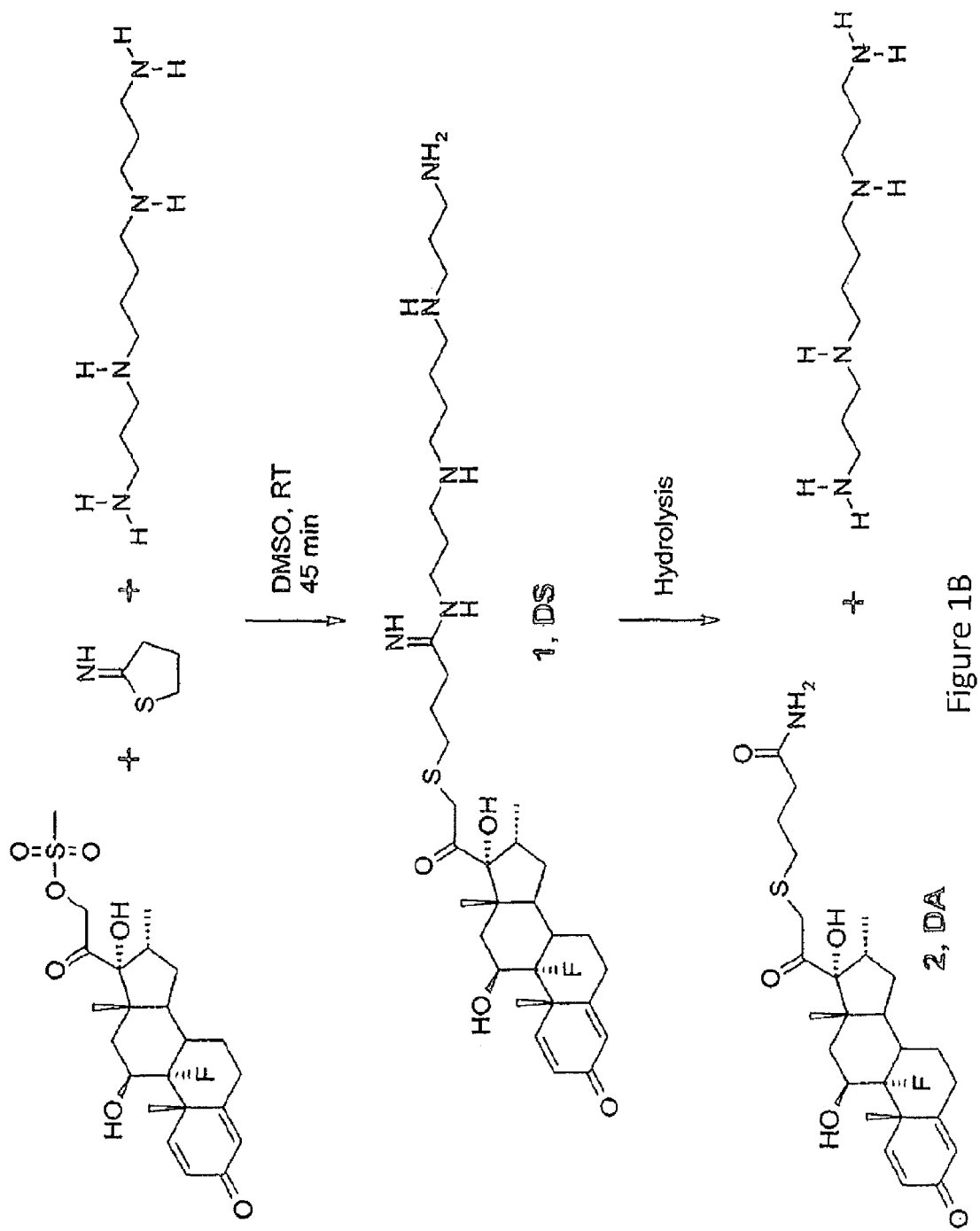
Figure 2:
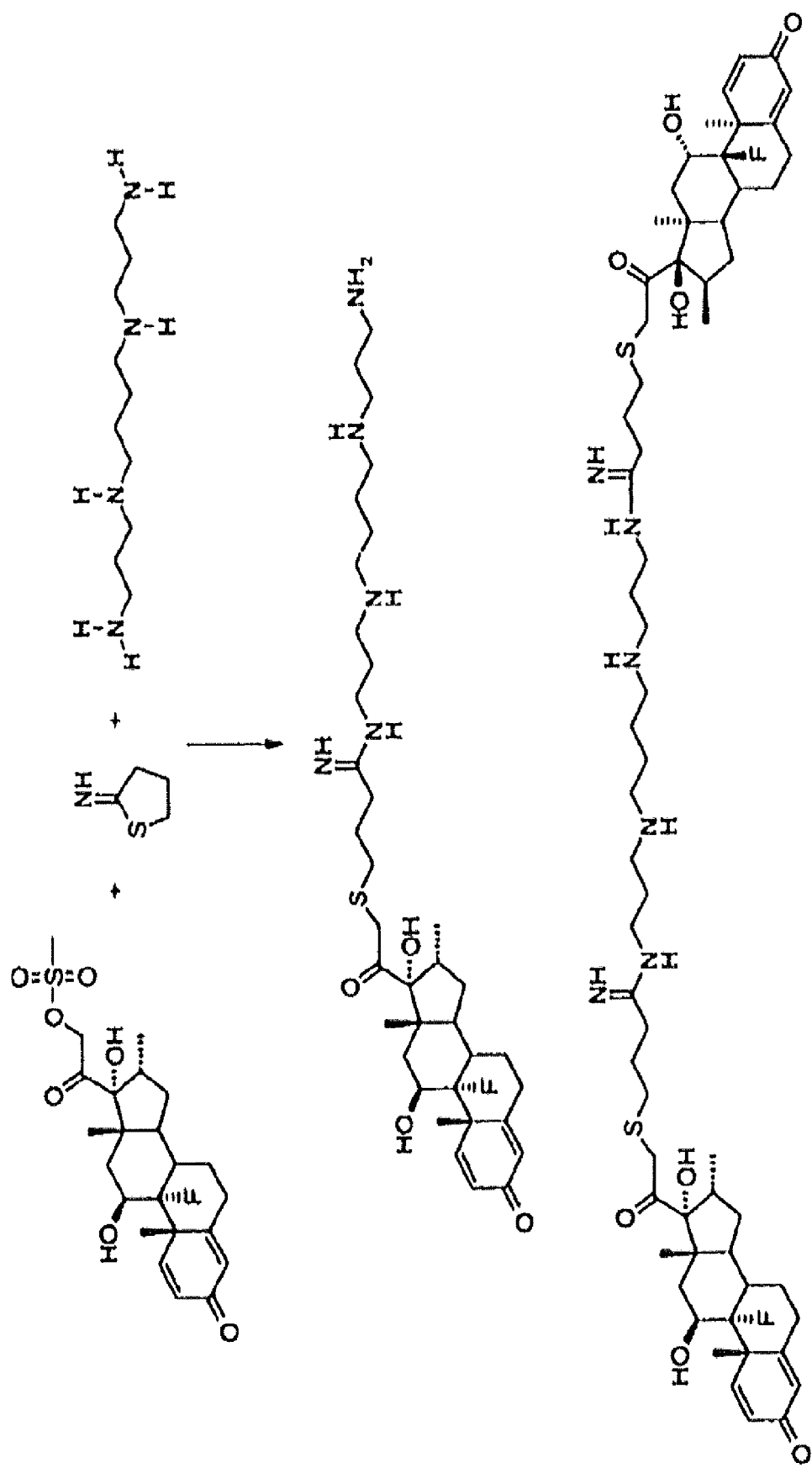
FIG. 2 depicts the structure of disubstituted spermine ($D_2S$), another product of the synthesis reaction. $D_2S$ is an amphiphilic dimer, disubstituted spermine, resulting from conjugation of dexamethasone to both primary amines on spermine. $D_2S$ exhibits the characteristic cationic charge of the primary reaction product at physiological pH due to the secondary amines retained from spermine and also has additional hydrophobicity relative to DS resulting from the additional dexamethasone moiety.

In one embodiment, the product of the synthesis reaction is dexamethasone-spermine (DS) molecule, resulting from conjugation of dexamethasone to a primary amine on spermine (see FIG. 1B). DS exhibits a cationic charge at physiological pH due to the amines retained from spermine. In another embodiment, the product of the synthesis reaction is an amphiphilic dimer, disubstituted spermine ($D_2S$), resulting from conjugation of dexamethasone to both primary amines on spermine (see FIG. 2). $D_2S$ exhibits the characteristic cationic charge of the DS product at physiological pH due to the secondary amines retained from spermine, but has additional hydrophobicity relative to DS resulting from the additional dexamethasone moiety.

Methods

The invention provides a method for decreasing or inhibiting a microbial infection or pathogenesis of a cell in vitro, ex vivo or in vivo, a symptom or pathology associated with a microbial infection or pathogenesis in vitro, ex vivo or in vivo, or an adverse side effect associated with a microbial infection or pathogenesis in vitro, ex vivo or in vivo.

In certain embodiments, the compounds of the invention can be used to inhibit (e.g., kill and/or inhibit growth and/or proliferation) certain microbes (e.g., certain bacteria, yeasts, fungi, molds, viruses, algae, protozoa, and the like) or group of microbes (e.g., gram-negative or gram-positive bacteria, particular genus, particular species, and the like.)

In one embodiment, the compounds of the invention can be used to inhibit at least one bacterium selected from among *Staphylococcus aureus, Escherichia coli, Klebsiella pneumoniae, Pseudomonas aeruginosa*, methicillin-resistant *Staphylococcus aureus*, and enterohemorrhagic *Escherichia*.

In one embodiment, the method includes treating a subject with a compound of the invention (e.g., D2S), wherein the subject is in need of treatment due to a microbial infection, in order to provide the subject with a beneficial effect or improvement.

In another embodiment, the method includes providing a subject with protection against a microbial infection or pathogenesis by administering a composition comprising a sufficient amount of a compound of the invention (e.g., D2S) to provide the subject with protection against a microbial infection or pathogenesis. In a further embodiment, a method of the invention includes treating a subject for microbial infection or pathogenesis by administering a composition comprising a sufficient amount of a compound of the invention (e.g., D2S) to treat the subject for the microbial infection or pathogenesis. Methods of the invention include administering a compound of the invention (e.g., D2S) prior to, concurrently with, or following contact of the subject with or exposure of the subject to a microbe; and administering a compound of the invention (e.g., D2S) prior to, concurrently with, or following development of a symptom or pathology associated with or caused by a microbial infection. In various aspects, a compound of the invention (e.g., D2S) is administered prior to (prophylaxis), concurrently with or following infection or exposure of the subject (therapeutic) to a microbe.

Methods of the invention therefore include providing a beneficial or therapeutic effect to a subject, for example, reducing, decreasing, inhibiting, delaying, ameliorating or preventing onset, progression, severity, duration, frequency or probability of a microbial infection or pathogenesis or one or more symptoms or pathologies associated with or caused by a microbial infection or pathogenesis; reducing, decreasing, inhibiting, delaying or preventing increases in microbial titer, load, replication, proliferation, or an amount of a microbial protein.

The present invention also includes method to treat or alleviate any infection of the oral cavity tissue. Infections of oral cavity tissue include, but are not limited to, halitosis, gingivitis, periodontitis, candidiasis (candidosis), periodontitis, dental caries, pulpitis, caries formation, and thrush. Oral tissue may be intact or may have one or more incisions, lacerations or other tissue-penetrating opening.

Bacteria in the oral cavity can produce volatile sulfur compounds (VSCs) which underlie oral malodor or halitosis. VSCs include hydrogen sulfide, methylmercaptan and dimethylmercaptan. The bacteria that contribute to this problem include: *Fusobacterium nucleatum, Treponema denticola, Tannereila forsythia* (formerly *Bacteroides forsythus*), *Prevotella intermedia, Porphyromonas gingivalis, Porphyromonas endodontalis*, and *Eubacterium* species.

Oral cavity infections that are related to dental plaque include caries development, gingivitis and periodontitis. While hundreds of bacteria have been detected in dental plaque, the most common bacteria that contribute to gingivitis and periodontitis are: *Actinobacillus actinomycetemcomitans, Campylobacter rectus, Eikenella corrodens* and seven anaerobic species, *Porphyromonas gingivalis, Bacteroides forsythus, Treponema denticola, Prevotella intermedia, Fusobacterium nucleatum, Eubacterium*, and spirochetes. *P. gingivalis*, a gram-negative anaerobe, is believed to be largely responsible for adult periodontitis. Various herpes viruses have been found to contribute to destructive periodontal disease. The bacteria that largely underlie caries formation are *Streptococcus mutan, Lactobacillus acidophilus, Actinomyces viscosus*, and *Nocardia* spp.

Administration

Various methods and assays have been described herein to synthesize and antimicrobial cationic steroid-polyamine composition and methods to add lipids to the antimicrobial cationic steroid-polyamine composition to arrive at a cationic lipid nonviral delivery vehicle having antimicrobial activity. In various embodiments, the antimicrobial cationic steroid-polyamine composition can be used to reduce the number of microbes populating a treatment site. In other various embodiments, the antimicrobial cationic steroid-polyamine composition of the invention can be used as a delivery vehicle, as well as to reduce the number of microbes populating a treatment site. Various assays have also been disclosed herein to demonstrate the ability of the antimicrobial cationic steroid-polyamine composition to kill bacteria. Moreover, various assays have also been disclosed herein to demonstrate the ability of the antimicrobial cationic steroid-polyamine composition to bind a compound and to deliver a compound to a cell. Preferably the cell is a mammalian cell, and more preferably the cell is a human cell.

In one embodiment of the invention, the antimicrobial cationic steroid composition is used to deliver a nucleic acid, steroid, drag, or compound to a cell. In one aspect of the invention the cell is selected from the group consisting of an endothelial cell, a mesenchymal cell, a neural cell, a fibroblast, neuron, a smooth muscle cell, a kidney cell, a liver cell, a myoblast, a stem cell, an embryonic stem cell, a hematopoietic stem cell, an osteoblast, a chondrocyte, a chondroblast, a monocyte, a neutrophil, a macrophage, a retinal nerve cell, and an epithelial cell. Preferably the cell is a mammalian cell. More preferably it is a human cell.

In one embodiment of the invention, the antimicrobial cationic steroid composition delivers a nucleic acid, steroid, drug, or compound to a tissue. In one aspect of the invention, the tissue comprises muscle, mucosa, epithelial, nerve, connective, blood, stromal, heart, liver, kidney, skin, brain, intestinal, interstitial space, bone, bone marrow, joint, cartilage, tendon, esophagus, gonad, cerebrospinal fluid, pancreas, spleen, ocular, nasal cavity, and hair tissue.

In various embodiments of the invention, the antimicrobial cationic steroid composition is delivered by at least one route of the group consisting of oral, intranasal, rectal, vaginal, intramuscular, topical, subdermal, sublingual, intraperitoneal, and intravenous.

The invention further relates to the use of the antimicrobial cationic steroid compositions of the invention in slow release therapies. In one embodiment of the invention, the antimicrobial cationic steroid composition or the nucleic acid, drug, compound, or molecule being delivered by the antimicrobial cationic steroid composition, may target molecules of interstitial and extracellular spaces by binding to said molecules. Such binding then allows slow release of the nucleic acid, drug, compound, or molecule at a local site.

In one embodiment, the antimicrobial cationic steroid composition useful for practicing the invention may be administered to the subject in a dose of between 1 ng/kg/day and 100 mg/kg/day. In another embodiment, the antimicrobial cationic steroid composition useful for practicing the invention may be administered to the subject in a dose of between 1 ng/kg/day and 100 g/kg/day.

Pharmaceutically acceptable carriers which are useful include, but are not limited to, glycerol, water, saline, ethanol, DMSO, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable, aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer compounds according to the methods of the invention.

Compounds which are identified using any of the methods described herein may be formulated and administered to a mammal for treatment of various diseases, disorders, or conditions described herein.

The invention encompasses the preparation and use of pharmaceutical compositions comprising a compound useful for treatment of various diseases, disorders, or conditions described herein. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals is the stratum column layer of the epidermis. The stratum contemn is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, chelating agents, bleaching agents, tyrosinase inhibitors and other known depigmentation agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, oral-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally-derived.

Liquid derivatives and natural extracts made directly from biological sources may be employed in the compositions of this invention in a concentration (w/v) from about 1 to about 99%. Fractions of natural extracts and protease inhibitors may have a different preferred rage, from about 0.01% to about 20% and, more preferably, from about 1% to about 10% of the composition. Of course, mixtures of the active agents, of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alphatocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate sails (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefor as would be known to those skilled in the art.

Controlled-release preparations may also be used and the methods for the use of such preparations are known to those of skill in the art.

In some cases, the dosage forms to be used can be provided as slow or controlled-release of one or more active ingredients therein using, for example, hydropropylmethyl cellulose, other polymer matrices, gels, permeable membranes, osmotic systems, multi layer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, mid mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A pharmaceutical composition of the invention may be prepared, packaged, or sold in a formulation suitable for oral or buccal administration. Suet a formulation may comprise, but is not limited to, a gel, a liquid, a suspension, a paste, a toothpaste, a mouthwash or oral rinse, and a coating. For example, an oral rinse of the invention may comprise a compound of the invention at about 1.4%, chlorhexidine gluconate (0.12%), ethanol (11.2%), sodium saccharin (0.15%), FD&C Blue No. 1 (0.001%), peppermint oil (0.5%), glycerine (10.0%), Tween 60 (0.3%), and water to 100%. In another embodiment, a toothpaste of the invention may comprise a compound of the invention at about 5.5%, sorbitol, 70% in water (25.0%), sodium saccharin (0.15%), sodium lauryl sulfate (1.75%), carbopol 934, 6% dispersion in (15%), oil of spearmint (1.0%), sodium hydroxide, 50% in water (0.76%), dibasic calcium phosphate dihydrate (45%), and water to 100%. The examples of formulations described herein are not exhaustive and it is understood that the invention includes additional modifications of these and other formulations not described herein, but which are known to those of skill in the art.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like, in particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the, animal, etc.

It will be recognized by one of skill in the art that the various embodiments of the invention as described above relating to methods of treating diseases, disorders or conditions, includes other diseases, disorders and conditions not described herein.

The invention further includes kits for treating a disease or disorder in an animal.

In accordance with the present invention, as described above or as discussed in the Examples below, there can be employed conventional chemical, cellular, histochemical, biochemical, molecular biology, microbiology and recombinant DNA techniques which are known to those of skill in the art. Such techniques are explained fully in the literature. See for example, Sambrook et al., 2001, Molecular Cloning—a Laboratory Manual, Cold Spring Harbor Press; Glover, (2001) DNA Cloning: a Practical Approach; Gait, (1984) Oligonucleotide Synthesis; Harlow et al., 1989 Antibodies—a Laboratory Manual, Cold Spring Harbor Press; Roe et al., 1996 DNA Isolation and Sequencing: Essential Techniques, John Wiley; and Ausubel et al., 1995 Current Protocols in Molecular Biology, Greene Publishing.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Synthesis and Hydrolysis of Antimicrobial Cationic Steroids DS and $D_2S$

There is a need in the art to be able to easily synthesize antimicrobial cationic steroids which, in some embodiments, are useful as vehicles for nonviral delivery of molecules to and into cells. A method to fulfill this need is disclosed in the present invention.

The Materials and Methods used in the present example are now described.

Large Scale, High Yield, Multi-Gram Synthesis of Steroid Mesylate Precursor for Conjugation A 200 mL Erlenmeyer flask equipped with a magnetic stir bar and a rubber septum was charged with 5 grams of dexamethasone (12.7 mmol, 1 equivalent) and 16 mL of anhydrous pyridine. The flask was cooled to 0° C. with an ice bath, and 1.2 mL of methanesulfonyl chloride was added. After 1 hour, 0.8 mL of additional methanesulfonyl chloride was added. At two hours, the solution was poured into 100 mL of cold 1M HCl, forming a precipitate. The precipitate was filtered and redissolved in 250 mL of ethanol, and precipitated into 250 mL of 1M HCl. The precipitate was filtered and recrystallized in ethanol, filtered, and dried under vacuum yielding 4.95 g (82.6%) of dexamethasone mesylate.

Synthesis of Antimicrobial Cationic Steroids

The 21-hydroxy group of dexamethasone is not required for anti-inflammatory activity, and therefore is an ideal choice for conjugation to a polycation (FIG. 1A) (Schimmer et al., 1996, in The Pharmacological Basis of Therapeutics, 1459-1485, eds. Hardman and Limbird, McGraw-Hill, New York). A one-pot reaction between spermine, 2-iminothiolane (Traut's reagent) and dexamethasone mesylate yielded the dexamethasone-spermine and disubstituted conjugates, (DS and $D_2S$, respectively) (FIG. 1B). Traut's reagent is selectively ring-opened by the primary amines (Hermanson, 1996, Bioconjugate Techniques, Academic Press) on spermine, forming a hydrolytically sensitive amidimide bond (Hermanson, 1996, Bioconjugate Techniques, Academic Press) between spermine and iminothiolane and a reactive thiolate anion that reacts with the α-keto mesylate on the 21 position of dexamethasone mesylate (Simmons et al., 1980, J. Org. Chem. 45:084-3088), yielding an α-keto thioether linkage between the dexamethasone and iminothiolane. Dexamethasone mesylate (prepared or received from Steraloids, N.H.) or dexamethasone (Steraloids, N.H.), 2-iminothiolane (Traut's reagent) (Pierce), spermine (Sigma), and ethanol or DMSO (Aldrich) were used as received. A total of 105 mg (223 µmol) of dexamethasone-mesylate, and 28.4 mg (206 µmol) of Trout's reagent were dissolved together in either DMSO or ethanol prior to addition of 31.9 µl (145 µmol of spermine at room temperature. The conjugation reaction was complete in 45 minutes by TLC. HPLC purification (60/40 0.1% TFA/acetonitrile, Hamilton PRP-1 column), evaporative solvent removal, and freeze-drying yielded both DS and $D_2S$ as white powders, $^1$H NMR of DS confirmed the presence of the 3-bisenone and 11- and 17-hydroxy groups required for glucocorticoid activity (FIG. 1A) as well as $^1$H signals from the conjugated spermine and the 21-α-keto thioether group. Hydrolysis of DS in 1M NaOH for 20 minutes resulted in the cleavage of the amidimide linkage between spermine and iminothiolane, forming a dexamethasone-amide (DA) (FIG. 1B), which has a 21-substituted butyl thioether amide sidechain on dexamethasone. For DA, FIG. 1B: Calc: C, 63.26; H, 7.35; N, 2.84. Found: C, 63.44; H, 7.27; N, 2.83. Water solubility: DS>100,000 mg/l; DA 60 mg/l; (dexamethasone 100 mg/l).

Large Scale, Multi-Gram, High Yield Synthesis of N-[3-({4-[(3-aminopropyl)amino]butyl}amino)propyl]-4-[(9-fluoro-11,17-dihydroxy-16-methyl-3,20-dioxopregna-1,4-dien-21-yl)sulfanyl]butanimidamide-TFA salt (1, Dexamethasone-Spermine, DS) and Disubstituted Spermine Product ($D_2S$)

A 1-L round-bottom flask equipped with a magnetic stir bar and rubber septum was purged with nitrogen and charged with 600 mL of USP-grade dry ethanol, 60 mL of anhydrous THF, 4.95 grams (10.5 mmol, 1.05 equivalents) of dexamethasone-mesylate and 10 grams (19.5 mmol, 4.95 equivalents) of spermine. 2-Iminothiolane, 1.38 grams (10 mmol, 1.0 equivalents) in 3 mL of water, was added dropwise to the solution over 5 minutes with vigorous mixing. The solution changed color from clear to clear light yellow. The reaction was monitored by TLC and by analytical HPLC. After three hours at room temperature, the TLC spot at $R_1=0$ (the charged DS) ($R_f=0.7$ minutes DS by analytical HPLC) was maximized, and dexamethasone-mesylate ($R_f$ 0.47, 2.8 minutes HPLC) spot minimized. The crude reaction mixture was diluted with 15.25 mL (198 mmol, 19.8 equivalents) of trifluoroacetic acid (or alternatively formic acid), forming a white precipitate (spermine tetra TFA salt or tetra-formate salt). Solvent was removed with a rotary evaporator and 50 mL of ethanol was added, forming a white precipitate (spermine-4TFA). The pH 3 solution was filtered twice to remove spermine acid salt, and ethanol was removed with a rotary evaporator. 50 mL of water was added to the yellow viscous oil, yielding a precipitate (dexamethasone and dexamethasone mesylate), and the solution was filtered through 0.2 μM filter to yield a clear yellow liquid. Water was removed with a lyophilizer over several days to yield dexamethasone-spermine and disubstituted spermine tetra-acid salts. Total yield ~30% for combined products).

TLC $R_f=0$, 50/50 Hexane/THF, analytical HPLC $R_f=0.7$ minutes, $^1$H NMR (500 MHz, DMSO) δ=6.23 (d, J=0.023, 1H, C2), 6.01 (s, 1H, C4), 5.33 (d, J=0.01, 1H, C17-OH), 5.04 (s, 1H, C11-OH), 4.14 (d, J=0.02, 1H, C11-OH), 3.63 (dd, J=0.39, 0.03, 2H, C21), 3.37 (s, 20H, Spermine), 3.27 (s, 2H, Spermine), 3.93 (s, 4H, Spermine), 2.61 (m, 1H, C6a), 2.37 (m, 1H, C6b), 2.33 (m, 1H, C8), 2.17 (d, J=0.02, 1H, C12), 2.1 (q, J=0.02, 1H, C14), 1.87 (m, 4H, Spermine), 1.78 (m, J=0.01, 1H, C7a), 1.63 (m, 2H, Spermine), 1.58 (m, 1H, C 15a), 1.48 (s, 3H, C19), 1.46 (s, 1H, C7), 1.07 (m, 1H, C15b), 0.87 (s, 3H, C18), 0.78 (d, 3H, C22); HRMS (FAB$^+$) $C_{38}H_{63}FN_5O_4S$: [M+H]$^+$ calcd 678.4428. found 678.4429.

Instrumentation/Semi-Preparative Purification

The LC-MS system consisted of a Shimadzu (Columbia, Md.) LC-20AB solvent delivery system and Shimadzu SIL-20A autosampler coupled to Shimadzu SPD-20A dual wavelength UV-Vis detector and Shimadzu LCMS 2010EV single quadrupole mass spectrometer. Purification was adapted from the method described in Gruneich et al. (2004, Gene Ther. 11:668-674). The semi-preparative separation system consisted of the Shimadzu instrument coupled to a Hamilton (Reno, Nev.) PRP-1 column (150 min×10 mm i.d., 10 μm particle size). The mobile phase flow rate was 4 mL/min with a starting ratio of 90% mobile phase A (water) and 10% mobile phase B (acetonitrile). The elution profile consisted of: (i) an isocratic step to 16% B for 30 minutes and (ii) 30% B for 30 minutes to separate the reaction products. Fractions were collected as either TFA or formate salts followed by complete solvent removal by lyophilization. Final products were dissolved in either nuclease free water or methanol/chloroform (50/50 vol %) at 5-6 mg/ml.

Analytical Characterization

Analytical characterization was performed with the Shimadzu instrument coupled to a Hamilton PRP-1 column (150 mm×2.1 mm i.d., 5 μm particle size). The mobile phase flow rate was 0.25 mL/min with a starting ratio of 90% mobile phase A (water) and 10% mobile phase B (acetonitrile). The elution profile consisted of: (i) an isocratic step to 16% B for 60 minutes and (ii) 30% B for 60 minutes to quantify purity. Mass spectrometry was performed on the eluent using electrospray ionization (ESI) in positive ion mode with a scanned m/z range from 160-2000. $^1$H and $^{13}$C NMR analysis was performed with a Bruker (location) AVANCE III 500 MHz instrument using a dual 5 mm cryoprobe or a Bruker DMX 600 using a 5 mm TXI 3 axis grad probe.

Other methods which were used but not described herein are well known and within the competence alone of ordinary skill in the art of chemistry, immunology, and cellular and molecular biology.

The Results of the experiments described in this example are now presented.

Synthesis of Cationic Dexamethasone Prodrug

There is a need in the art for a nonviral cationic lipid delivery vehicle which can deliver such molecules as nucleic acids or drugs to cells, interstitial sites, organs, or tissues. Further, there is a need in the art for a cationic steroid compositions which can prevent and/or ameliorate inflammation. This invention satisfies this need.

Example 2

Molecule Delivery In Vitro with a Nonviral Cationic Steroid Delivery Vehicle

The Materials and Methods used in the present example are now described.

Cell Culture and Lipofection

Bovine aortic endothelial cells (BAEC, passage 4-13) were passaged at a 1:3 split to 24-well culture plates, and then grown to dense confluence before lipofection. Growth medium was Dulbecco's modified Eagle's medium (DMEM) containing 10% heat inactivated charcoal-filtered (to remove steroid hormones) fetal calf serum (Hyclone), 0.30 mg/ml glutamine, 150 U/ml penicillin, and 0.15 mg/ml streptomycin (Gibco). 293 cells were grown under identical conditions. The plasmids pEGFP-N3 and pGRE-SEAP (Clontech) were used for expression of EGFP or secreted alkaline phosphatase under the regulation of CMV or GRE promoters, respectively. In some experiments, Lipofectamine reagent (Invitrogen) containing 2:1 (μg:μg) mixture of polycationic lipid 2,3-dioleyloxy-N-[2(sperminecarboxamido)ethyl]-N,N-dimethyl- 1-propanaminium trifluoroacetate (DOSPA):DOPE was used according to manufacturer's instructions. In other experiments, Lipofectamine 2000 (Invitrogen), in a 1:1 (wt) ratio with nucleic acid, was used according to the manufacturer's instructions.

For fluorescence microscopy and flow cytometry, pEGFP-N3 plasmid (Clontech, Palo Alto, Calif.) was used to generate GFP as the fluorescent reporter transgene protein. Cells were transfected in 6-well plates with each condition in duplicate. One day after GFP transfection, cells were imaged and then harvested in 500 ul PBS and kept on ice until analysis. A BD Biosciences (Franklin Lakes, N.J.) FACSCalibur flow cytometer was used to obtain fluorescence data with 50,000 counts recorded per condition.

For the luminescence assays, pGL4.75 plasmid (Promega, Madison, Wis.) was used to generate militia luciferase as the reporter transgene protein. Cells were transfected in 96-well plates with 8 replicates of each condition. To measure transgene expression, EnduRen Live Cell Substrate (Promega) was added 24 hours after transfection and luminescence was measured 90 minutes following addition of the reagent. Cell viability was determined by adding an equal volume of Cell Titer Glo (Promega) and measuring luminescence 30 minutes after addition. Luminescence in both assays was measured with an EnVision Multilabel Plate Reader (Perkin Elmer, Wellesley, Mass.).

Preparation and Characterization of Lipid Assemblies and Lipoplexes

To form the DS:DOPE lipid solution, 67 µl of a 10 mg/ml solution of DS in ethanol and 27 µl of a 50 mg/ml solution of DOPE in ethanol were vortexed together. After solvent evaporation with a $N_2$ stream, 1 mL of sterile Millipore water was added to the lipid film and the solution was sonicated for 10 minutes. The solution (2 µg of lipid per µl of water) was stored at 4° C. and retained lipofection activity for over 6 months (data not shown). The hydrodynamic diameter of DS/DOPE (1 µg/2 µg) obtained by dynamic light scattering (DynaPro 99 instrument) was 70 to 150 nm without DNA, while lipoplexes with 1 µg DNA and 0 to 20 equivalents of DS and 0 to 20 equivalents of DOPE had sizes ranging from 200 to 500 nm.

Fluorescence GFP Measurement

For lipofection, a solution of DS/DOPE in 125 µl Opti-MEM I (Gibco) was mixed with a solution of DNA in 125 µl OptiMEM I, incubated for 30 to 60 minutes, and then overlaid on BAEC cells for 2 hours, followed by PBS rinse and addition of growth media. Fluorescence was measured after 48 hours. At lipid concentrations exceeding charge ratios of 6:1 DS:DNA, the formulations began to display cytotoxicity in BAEC as indicated by altered morphology. EGFP expression of transfections was monitored in duplicate (FIG. 2A) or triplicate (FIG. 2B) with a fluorescent plate reader (Lab-systems Fluoroskan Ascent; 485 nm/538 nm filter pair) with background subtraction using the autofluorescence of non-transfected BAEC. EGFP expression was calibrated using 0 to 200 ng recombinant GFP (Clontech) in 750 µl PBS. In assays of EGFP in lysates, lipofected cells were trypsinized, pelleted (200×g, 8 minutes), resuspended in 150 µl PBS, and subjected to 3× freeze/thaw at −78° C. The lysate was centrifuged at 13,500 RPM (5 minutes) in an Eppendorf Minifuge. Supernatant was collected, and pooled with supernatant from PBS washed and pelleted cells (total volume 750 µl), and EGFP fluorescence was measured (Ex 485, Em 515; SLM fluorometer). In some experiments, flow cytometry of lipofected and trypsinized cells expressing EGFP was performed at the University of Pennsylvania Flow Cytometry Core Facility using a FACSCalibur instrument.

The Results of the experiments described in this example are now presented.

In Vitro Gene Delivery with Cationic Steroids

Figure 3:
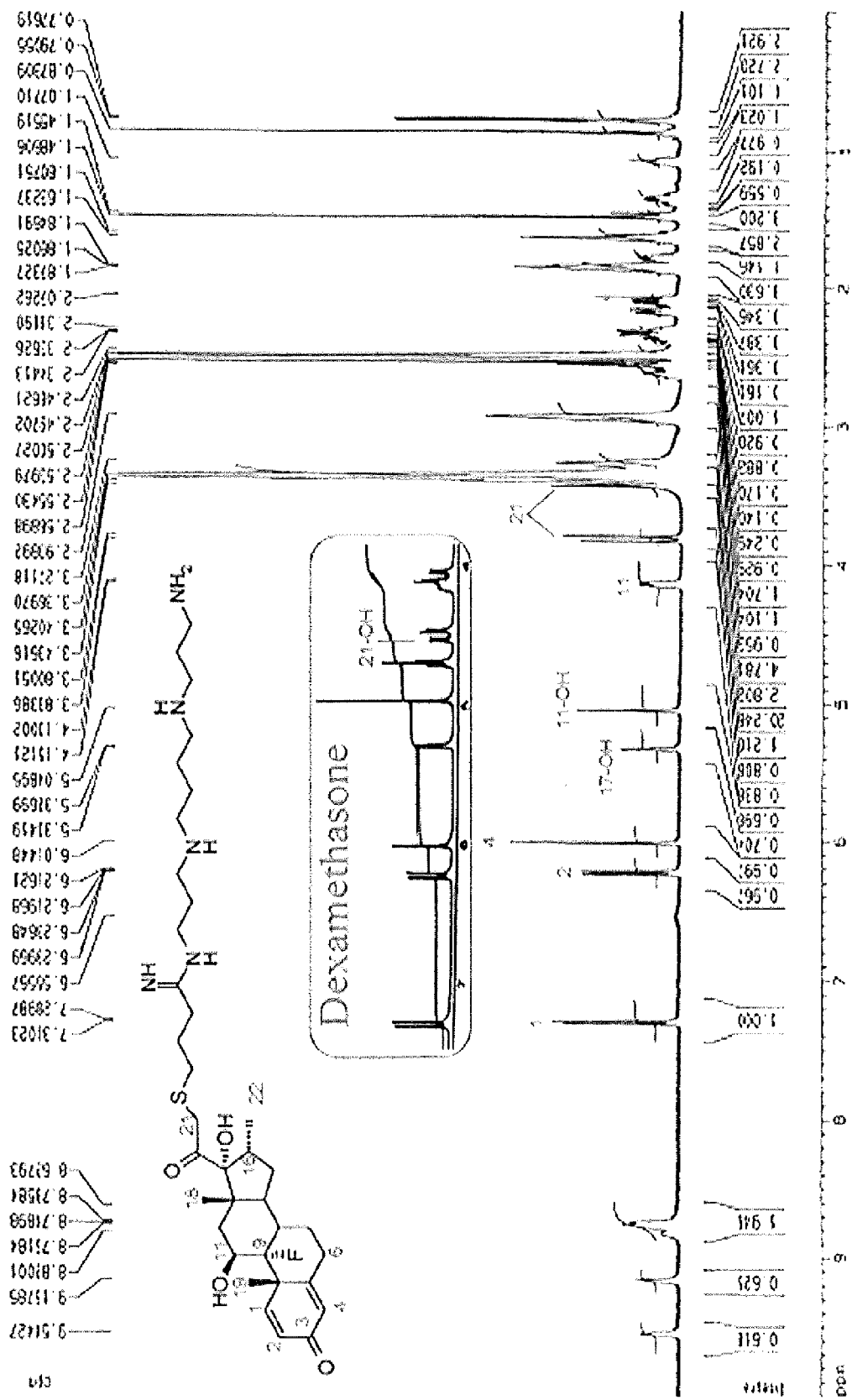
FIG. 3 depicts the results of Nuclear Magnetic Resonance analysis of DS.

Using the neutral lipid dioleylphosphatidylethanolamine (DOPE) and 1 µg plasmid/well, we measured gene expression obtained with varying amounts of DS (0 to 20 µg) and varying amounts of DOPE (0 to 20 µg (FIG. 2A). In the case where neither DS nor DOPE was present, Lipofectamine was used (6 µg/µg-DNA) as a benchmark. The mass ratio of 1:2 of DS:DOPE (light bars, FIG. 2A) provided high EGFP expression while minimizing the use of the DS conjugate and minimizing the total lipid load below 10 µg total lipid/µg DNA. In a separate set of experiments maintaining the DS/DOPE mass ratio constant at 1:2, the amount of DS relative to DNA was systematically varied from 1 to 10 charge equivalents (0.9 to 9 µg DS per µg DNA), assuming an average charge of the spermine of DS to be 3.8 per molecule (Geall et al., 2000, Bioconjug. Chem. 11:314-326) and no net charge contribution from DOPE. The optimal lipofection plateaued at a charge ratio of 6 DS:1 DNA, giving more than 10-fold increase in the amount of transgene expression relative to Lipofectamine reagent. Increases beyond a charge ratio of 6:1 DS:DNA provided no increase in expression (FIG. 2B). To test if gene transfer activity of DS was merely associated with the DNA binding ability of spermine and the hydrophobic character of dexamethasone, DNA was combined with spermine, dexamethasone, and DOPE (all unconjugated) using the same molar ratios and concentrations as in the conjugated DS/DOPE transfection (FIG. 2D). Only when the dexamethasone was conjugated with spermine was EGFP expression detected (FIG. 2E). Spermine alone or dexamethasone alone had no detectable gene transfer activity. Using a flow cytometry cutoff of 100 F.I. to define percent transfection (Subramanian et al., 1999, Nat. Biotech. 17:873-877), a 4.3-fold increase was observed in percent transfection over Lipofectamine from 5.9% to 25.5% (FIG. 3). Lipofection of sub-confluent (proliferating) BAEC with DS/DOPE yielded a 4.6-fold increase in percent transfection over Lipofectamine from 16.0% with Lipofectamine to 73.8% lipofection with DS/DOPE (data not shown). Although hydrolysis of DS to DA is accelerated in 1M NaOH, the amidimide bond in DS appeared relatively stable in neutral pH when formulated with DOPE, since DS/DOPE formulations stored for six months at 4° C. in water retained their lipofection activity.

Synthesis and Use of Other Cationic Steroids in Delivery Vehicles

The conjugation of spermine to steroids was carded out to create molecules useful for DNA transfer to mammalian cells. 21-chloro-17hydroxyprogesterone, cholesterol tosylate, hydrocortisone mesylate, or 17 α-mesylate-estradiol-3-acetate was mixed with DMSO and Traut's reagent followed by addition of spermine. The resulting cationic steroids displayed gene transfer activity when used with the neutral lipid, DOPE, on 293 cells.

Figure 6:
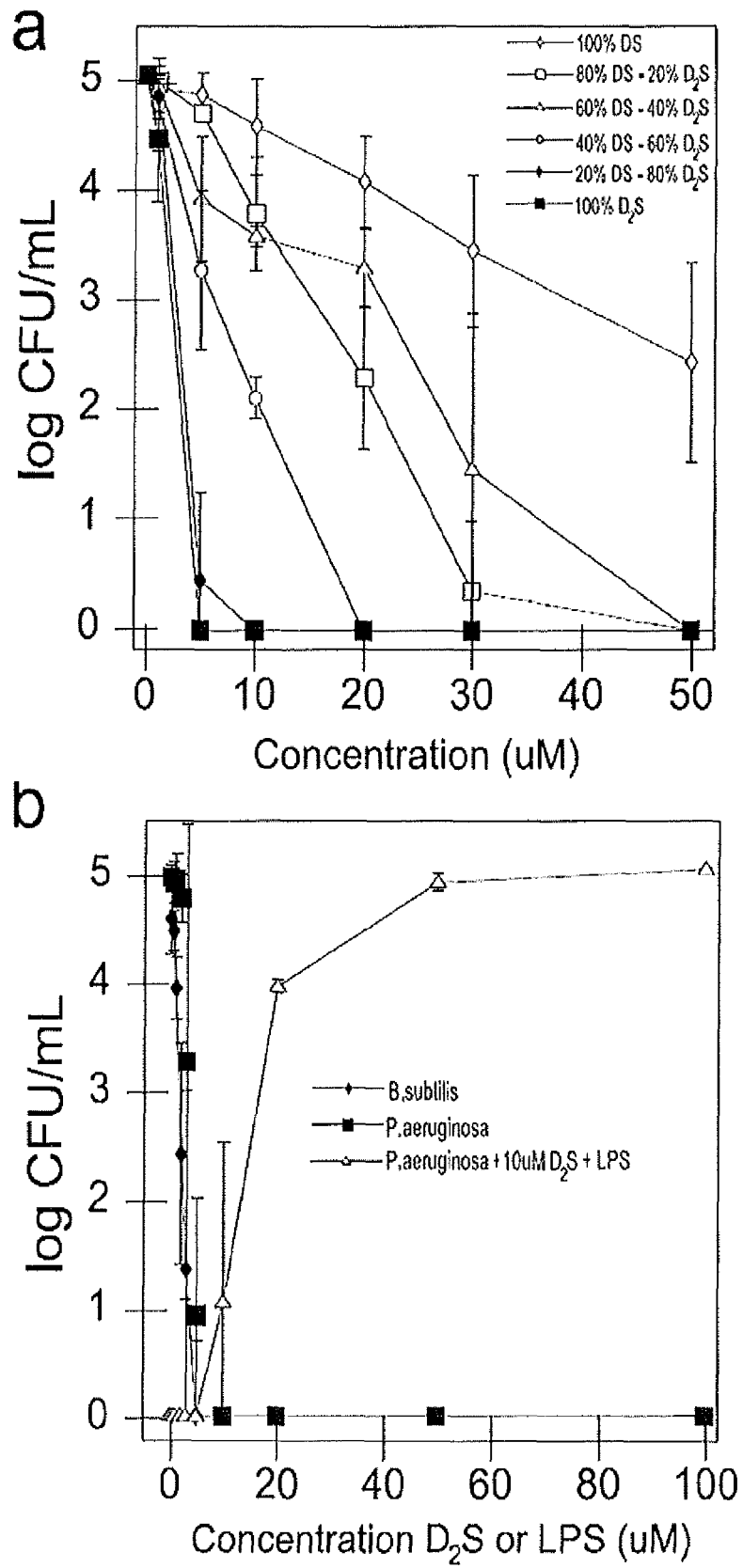
FIG. 6, comprising
Figure 6:
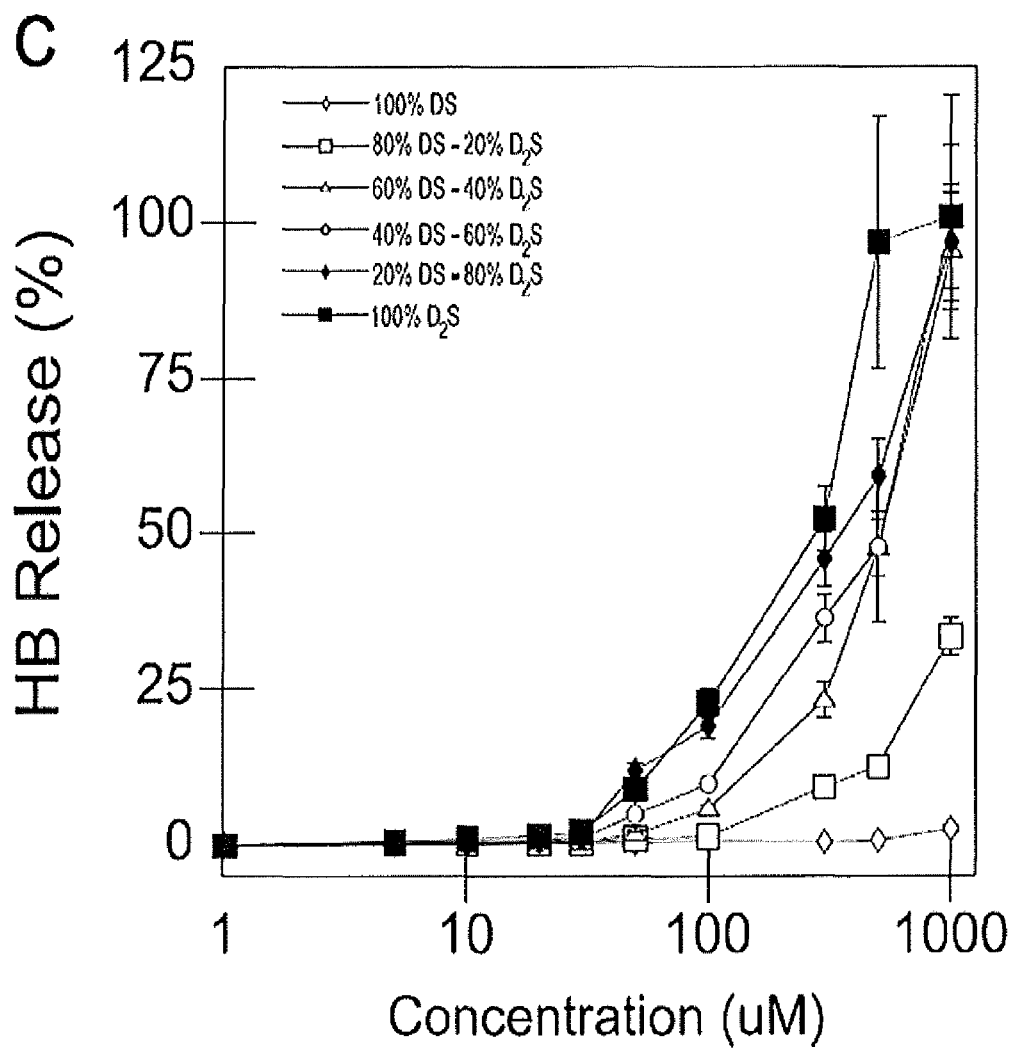

Other compounds which were coupled with spermine and tested on bovine aortic endothelial cells include 11-deoxycortisone, 11-deoxycortisol, cortisol, and corticosterone. Twenty-one formulations were tested and had varying effects on EGFP expression (see FIG. 6).

Use of Other Cationic and Hydrophobic Compounds

Based on the structural resemblance of tamoxifen (estrogen antagonist) and 4-hydroxytamoxifen to other cationic steroids (e.g., dexamethasone-spermine) or cationic cholesterol derivatives, the gene transfer activity of tamoxifen and 4-hydroxy tamoxifen was measured. To examine whether tamoxifen or 4-hydroxytamoxifen (a more active metabolite) can function as nucleic acid transfer reagents, drug was formulated with DOPE at various ratios and then mixed with DNA. GFP expression was measured in 293 cells and the results indicate that these additional steroids can be used as well in a delivery vehicle of the invention.

A number of pharmacological drugs have lipophilic and cationic groups. These compounds are in a class of molecules that can bind DNA and have gene transfer activity in the presence or absence of neutral lipids such as DOPE or cholesterol. Representative examples of other drugs that reside in the class of molecules which are cationic and lipophilic include, but is not limited to rantidine HC, propoxyphese-N/APAP, tamoxifen, verapamil SR, triamterene w/HCTZ, trimox, acyclovir, cyclobenzaprine, methylphenidate, amitriptyline, trimethoprim/sulfa, ipratropium bromide, methotrexate, diltazem CD, norvasc, prozac and sarafem, vasotec, zestril, effexor, prinivil, imitrex, serevent, zoloft, and paxil.

These results describe a new approach to nonviral nucleic acid and drug delivery by using a novel cationic prodrug or drug vehicle. Dexamethasone, a potent glucocorticoid recognized to enhance gene delivery in vivo, was conjugated with spermine via an iminothiolane linkage. This molecule was designed to combine the gene delivery properties of the clinically relevant cationic lipids such as DC-Chol, DMRIE, DOTMA, and GL-67, with the added functionality of hydrolyzing to release pharmacologically active drug. This procedure yielded a pharmacologically active prodrug that facilitates nucleic acid and drug packaging and delivery. The use or pharmacologically active cationic steroids also allows the exploitation of anionic biopolymers such as glycosaminoglycans in the body to servo as natural occurring depots for local drug delivery.

Example 3

Transfection

Transfection experiments were designed and performed to assess the gene transfer efficiency of novel cationic lipids by using two distinct cells lines (i.e., BAEC and A549) with an optimized commercially available product as a positive control. Both cell lines were cultured at 37° C. and 5% $CO_2$ in DMEM (Invitrogen, Carlsbad, Calif.) supplemented with 10% fetal bovine serum (Invitrogen), 2% penicillin/streptomycin (Mediatech, Inc., Manassas, Va.), and 1% L-glutamine (Mediatech) prior to transfection which was carried out in Optimem. All experiments were executed with cells seeded 24 hours prior to transfection at 50-75% confluence. Lipofectamine 2000 (Invitrogen) was used as a positive control for all transfection experiments and optimized independently for transfection efficiency with minimal toxicity for each cell line. A 1:1 (wt) ratio with plasmid was used for BAECs and a 3:1 (wt) ratio with plasmid was used for A549 cells following the manufacturer's instructions. Although higher ratios of Lipofectamine 2000 to DNA were tested (data not shown), a ratio of 1:1 was used for BAECs and 3:1 for A549 cells since these ratios maximized transfection efficiency while minimizing toxicity for this product under these conditions in each cell line. Plasmid DNA without any cationic lipid was used as the negative control. Due to the observed shill in net surface charge resulting from different compositions of the experimental cationic lipids, three charge ratios were tested in order to assess how excess lipid/cationic charge affected transgene expression. Plasmid pGL4.75 (Promega, Madison, Wis.) was used to generate renilla luciferase as the reporter transgene protein. Cells were transfected in 96-well plates with 8 replicates of each condition. To measure transgene expression, EnduRen Live Cell Substrate (Promega) was added and luminescence was measured 90 minutes following addition of the reagent. Cell viability was determined by adding an equal volume of Cell Titer Glo (Promega) and measuring luminescence. Luminescence in both assays was measured with an EnVision Multilabel Plate Reader (Perkin Elmer, Wellesley, Mass.). Error bars represent standard deviations from 8 replicates of each condition. Significant increases in luminescence from transfection with respect to the positive control (Lipofectamine 2000) were calculated using the Mann—Whitney U-test (*$P \leq 0.05$). RLU=Relative Light Unit.

Figure 5:
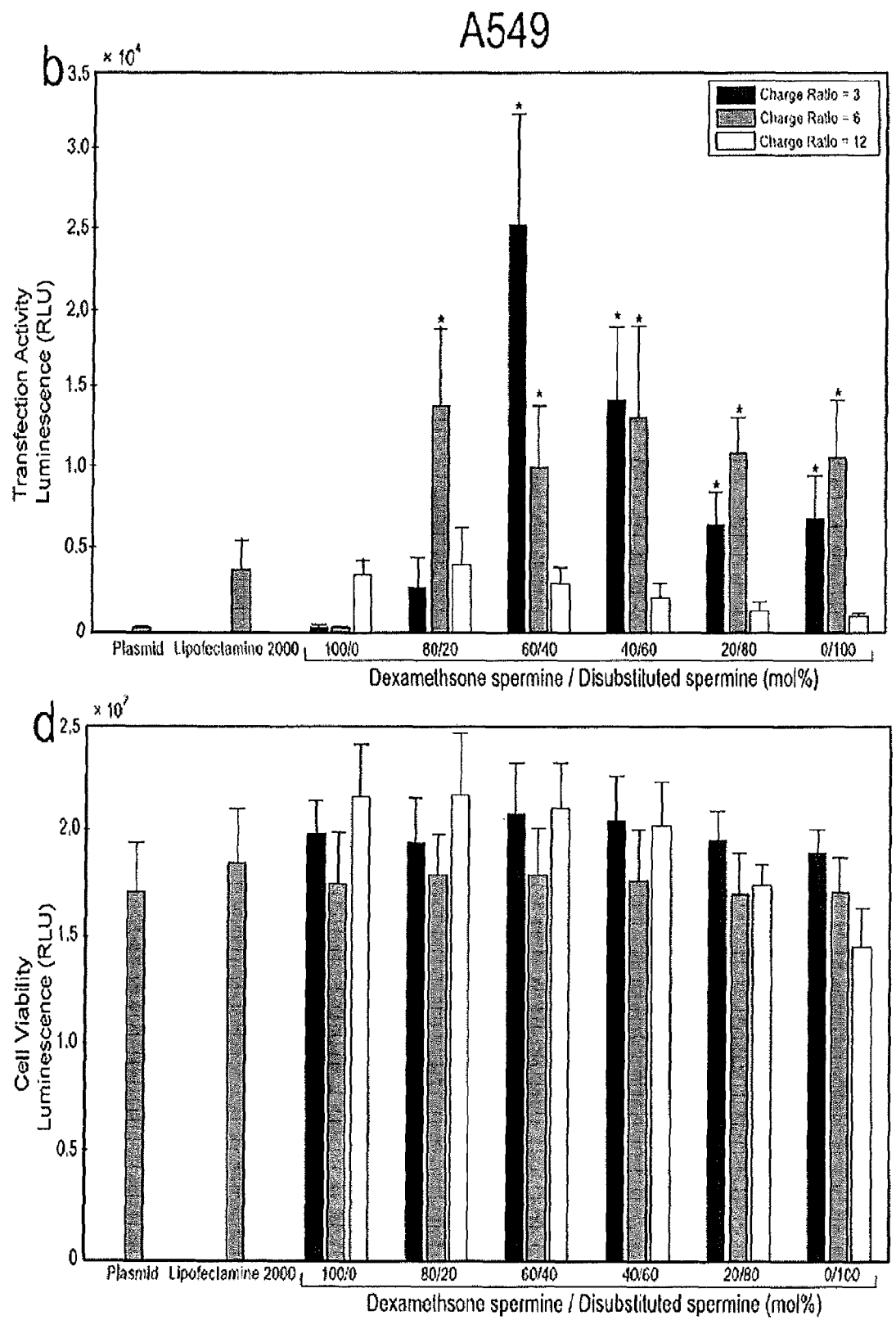
FIG. 5, comprising

Lipofection of BAEC and A549 cells, a human carcinoma alveolar epithelial cell line, were carried out under identical conditions in both cell lines and the transfection activity of mixtures of DS and $D_2S$ showed a clear dependence on cell-type as shown in FIGS. 5a and 5b. Higher transgene expression was measured with mixtures of DS and $D_2S$ than either compound independently, however; optimal activity was observed at different charge ratios and lipid compositions in each cell type. Peak activity in BAECs was 3-fold greater than control (CR=12 and 20 mol % $D_2S$), whereas A549 cell transfection showed a maximum 7-fold increase in transgene expression (CR=3 and 40 mol % $D_2S$). A second transfection experiment was performed with BAECs using GFP as the reporter (Supplementary material) with fluorescent images and flow cytometric data confirming the finding of peak transfection activity with a mixture of DS and $D_2S$. Cell viability (FIGS. 5c and 5d) decreased to some extent with $D_2S$ concentration and charge ratio (12-15% maximum) compared to negative controls. It is important to note that the maximum enhancement in transgene expression observed in both cell lines was achieved without compromising cell viability and that the 3 to 7-fold increase over a common lipofection reagent indicates a significant improvement.

Due to the number of variables that can affect liposome-mediated gene delivery, physical properties are commonly studied to determine if they correlate with the resulting activity and to further develop structure-activity relationships for vector design. (Ma et al., 2007, J Control Release, 123:184-194) Particle size and zeta potential were measured as a function of the mixed lipid composition since these properties have been found to correlate with gene transfer activity. (Ross and Hui, 1999, Gene Ther, 6:651-659; Salvati et al., 2006, Biophys Chem, 121:21-29) A correlation was observed between shifts in both parameters with the peak transfection activity. This apparent association between physical parameters and transfection activity could be due to a number of factors including the morphology of the lipoplexes, heterogeneity of lipids between the liposomal surfaces, or packaging of the plasmid DNA; however, a clear relationship was determined to exist between size, zeta potential, and transfection activity over the experimental range. Enhancement in gone delivery and optimal biophysical parameters were observed in both cell lines with mixtures of DS and $D_2S$ indicating that improvement in vector design can be achieved without the generation of new molecular structures.

Figure 7:
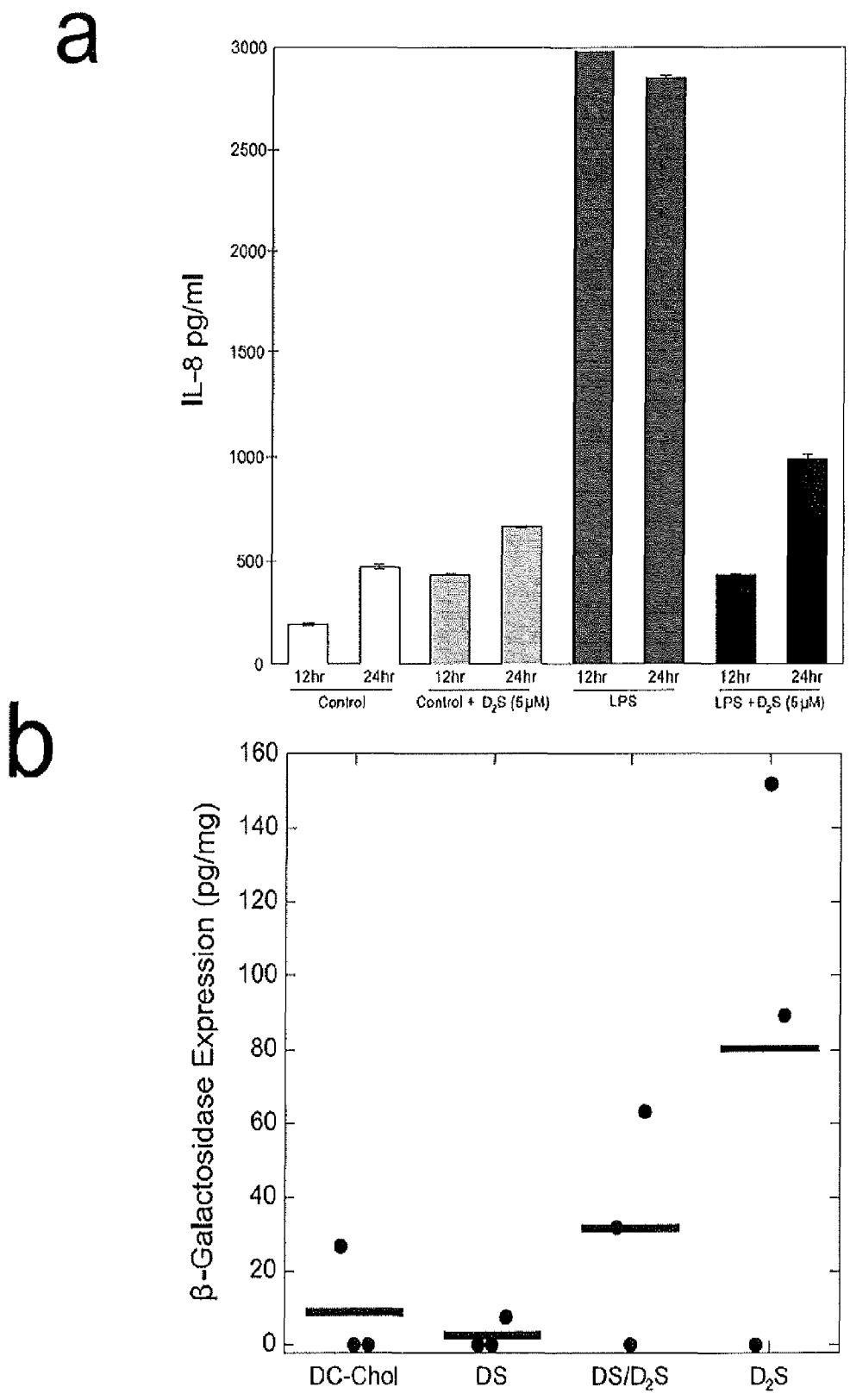
FIG. 7, comprising

The efficiency of these gene delivery vectors in vivo was assessed with an expression plasmid encoding a LacZ transgene β-galactosidase ((β-gal)). DC-Chol was used as the positive control in this experiment since this cationic lipid has been shown to facilitate plasmid transfection in vivo and can be re-administered. (Hyde et al., 2000, Gene Ther, 7:1156-1165) Minimal transgene expression was detected in lung homogenates for both DC-Choi and DS lipoplexes, while the 60/40 mol % mixture of DS and $D_2S$ liposomes exhibited higher expression levels (FIG. 7b). Due to the volume limitation for 1N administration in mice (50 μl), a lower total charge ratio (CR=0.5) compared to the in vitro studies was required in order to maximize total plasmid delivery (50 μg); however, measurable transgene levels confirm that $D_2S$ lipoplexes as well as mixtures of DS and $D_2S$ can facilitate plasmid gene delivery to the lung.

Figure 9:
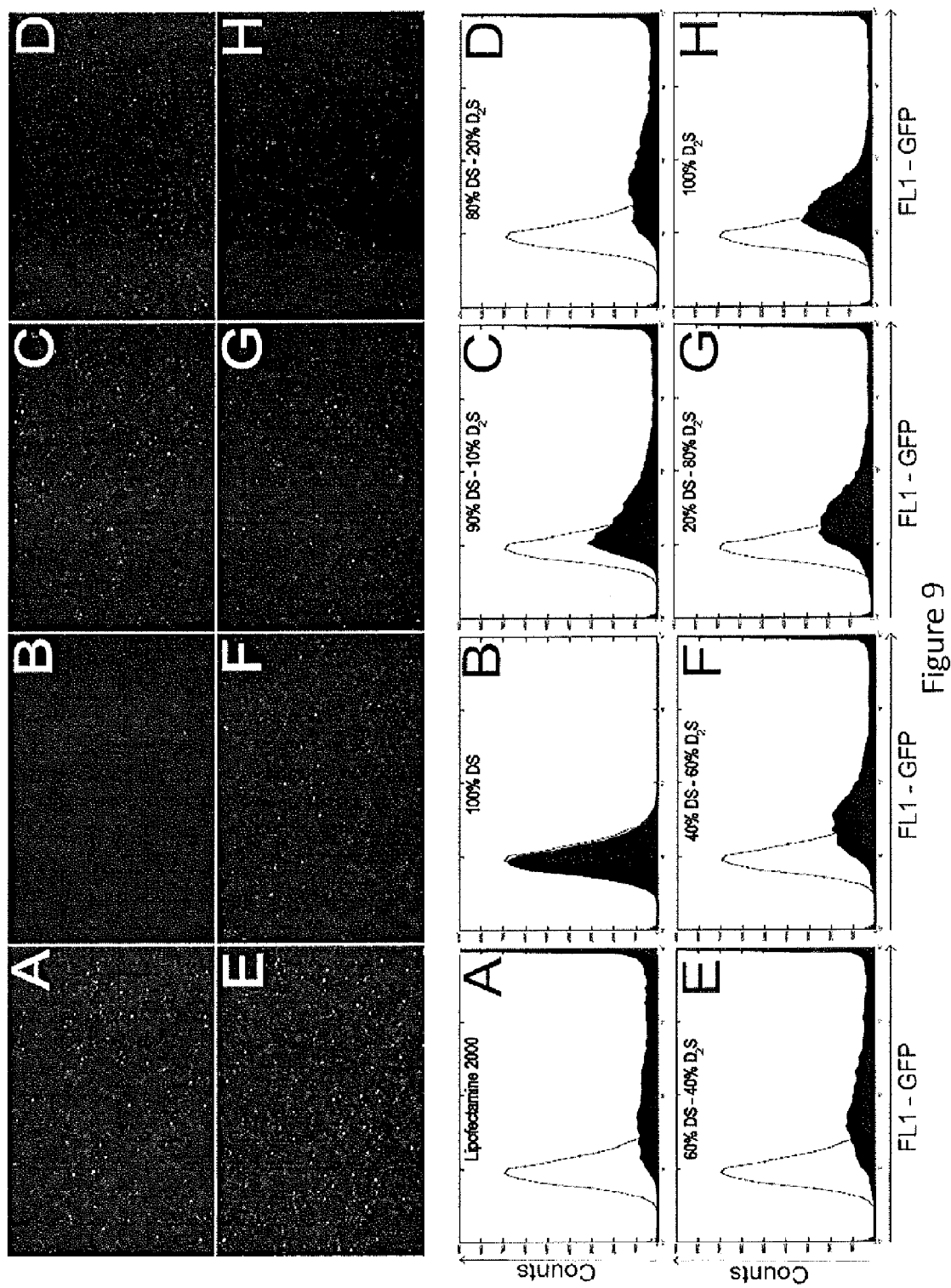
FIG. 9, comprising
Figure 9:
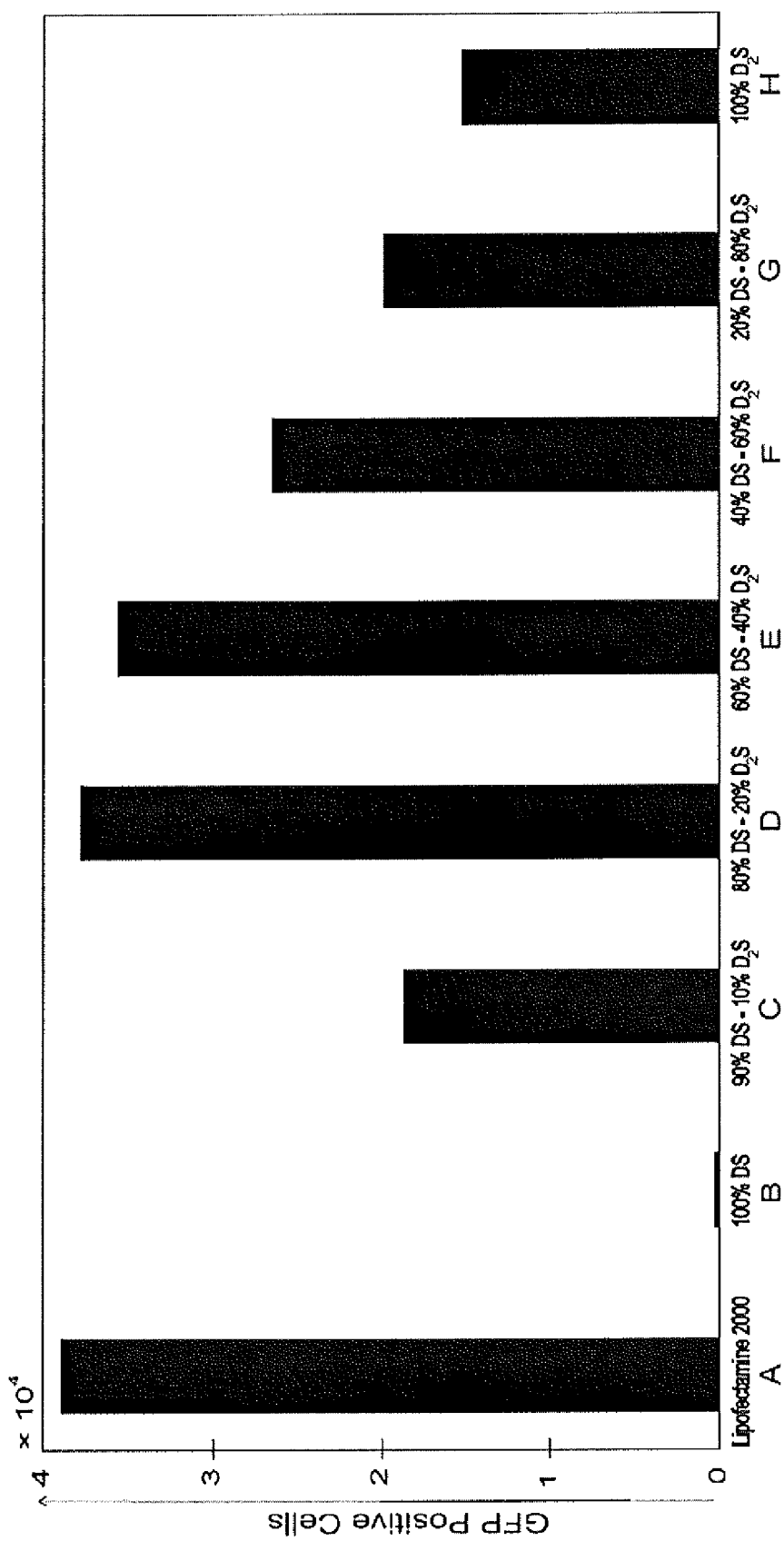

Experiments assessing the transfection of BAECs with DS and $D_2S$ using GFP transgene at a charge ratio of 6:1 at 24 hours were also conducted. Fluorescent images and flow cytometry data shown with experimental data (black area) over negative control (white area) for each condition. Histogram of number of gated positive transfected cells based on negative control. Lipofectamine 2000 control (FIG. 9A), 100/0 mol % $DS/D_2S$ (FIG. 9B), 90/10 mol % $DS/D_2S$ (FIG. 9C), 80/20 mol % $DS/D_2S$ (FIG. 9D), 60/40 mol % $DS/D_2S$ (FIG. 9E), 40/60 mol % $DS/D_2S$ (FIG. 9F), 20/80 mot % $DS/D_2S$ (FIG. 9G), 0/100 mol % $DS/D_2S$ (FIG. 9H). For fluorescence microscopy and flow cytometry on BAECs, pEGFP-$N_3$ plasmid (Clontech, Palo Alto, Calif.) was used to generate GFP as the fluorescent reporter transgene protein. BAECs were transfected in 6-well plates with each condition in duplicate. One day after GFP transfection, cells were imaged and then harvested in 500 μl PBS and kept on ice until analysis, A BD Biosciences (Franldin Lakes, N.J., USA) FACSCalibur flow cytometer was used to obtain fluorescence data with 50000 counts recorded per condition.

Example 4

Antimicrobial

The amphipathic nature of lipids used for transfection has been shown to have deleterious effects at high concentrations due to disruption of host cell membranes, but might also potentially beneficial effects due to preferential disruption of bacterial membranes, which unlike eukaryotic membrane expose highly anionic lipids at their surface. It was theorized that $D_2S$ could be a more effective destabilization agent of cellular membranes than DS, which would explain how moderate concentrations in combination with DS could lead to optimal transfection activity. These theories were tested by measuring antimicrobial activity to determine the relative membrane disruption potential for DS, $D_2S$, and mixtures of these compounds. Addition of the cationic lipid mixtures to suspensions of the gram negative bacterium Escherichia coli MG1655 was performed to evaluate antimicrobial activity and differences were observed across the series of compositions tested (FIG. 6a). A gram-negative strain of bacteria was chosen to test the range of lipid mixtures since this is typically a more challenging test for antimicrobial killing due to the permeability barrier of the second bacterial membrane. The number of colony forming units was determined using a conventional killing assay and showed that $D_2S$ is the most active destabilization agent, since mixtures with increasing concentration of DS led to decreased antibacterial activity. No bacterial growth was observed upon addition of 50/1 of $D_2S$, which was equivalent to the activity of the cathelicidin peptide LL37 and the ceragenin CSA-13 (data not shown) used as positive controls in the assay (See Salunke et al., 2004, J Med Chem 47:1591-1594; Chin et al., 2007, Antimicrob Agents Chemother, 51:1268-1273). $D_2S$ antibacterial activity against the gram-positive B. subtillis and an additional gram-negative bacterium P. aeruginosa PA01 demonstrated killing activity at the same (P. aeruginosa) or lower (B. subtillis) concentrations compared to E. coli, demonstrating that both gram-positive and gram-negative bacteria are in the spectrum of bactericidal activity (FIG. 6b). Additionally, bactericidal activity of $D_2S$ was found to be compromised in the presence of purified LPS (E. coli) indicating a specific interaction between those two molecules (FIG. 6b) likely due to an electrostatic interaction between the cationic lipid and the negatively charged bacterial endotoxin. The in vivo antibacterial activity of $D_2S$ was assessed by utilizing P. aeruginosa Xen5, a mucoid strain that constitutively expresses a luminescent protein (lux) during normal metabolic function. Bioluminescent imaging was utilized to assess bactericidal activity and imaging before and after D2S injection in lung confirmed rapid inhibition of bacterial metabolic activity (FIG. 7c). Bacterial luminescence was not affected in other areas providing evidence that the compound was successfully delivered to the lung.

Experiments were conducted assessing the concentration kill curves for E. Coli MG 1655 with mixtures of DS and $D_2S$ (FIG. 6a), and for B. subtillis, P. aeruginosa PA01, and P. aeruginosa PA01 in the presence of purified LPS (FIG. 6b). A single colony of Escherichia coli MG1655, Bacillus subtillis (ATCC 6051), or kanamycin-resistant Pseudomonas aeruginosa PAOI was selected from a LB plate and grown to mid-log phase (OD600~0.3) in 2 mL of LB medium (Becton-Dickinson, Cockeysville, Md.). One milliliter of the bacterial suspension was centrifuged at 5000 rpm for 5 minutes at RT, and the bacterial pellet was resuspended in PBS. Serial dilutions of DS, $D_2S$, LL-37 peptide, and the ceragenin CSA-13 were mixed with the diluted bacterial suspension in 0.1 ml aliquots. The tubes were then incubated at 37° C. for one hour and transferred to ice. Duplicate 10 μl aliquots of 10-fold dilutions (undiluted, 1:10, 1:100, 1:1000) of these mixtures were plated on sectors of LB agar or Pseudomonas isolation agar plates, and plates were incubated overnight at 37° C. The number of colonies in the duplicate samples at each dilution was counted the following morning, and the colony forming units (CFU) of the individual mixture were determined from the dilution factor. To assess $D_2S$ scavenging binding potential, LPS from E. coli (Sigma) was added to the bacterial suspensions and incubated for 1 hour. Error bars represent standard deviations from 3.5 replicates for each condition. Red blood cell lysis in response to treatment with DS and $D_2S$ was also assessed (FIG. 6e). The hemolytic activity of $D_2S$ against human red blood cells (RBC) was tested using their suspension prepared from flesh blood (Ht~5%). $D_2S$ dissolved in PBS was added to RBC suspensions and the incubation was continued for 1 hour at 37° C. The samples were then centrifuged at 1300×g for 10 min for hemoglobin release analysis. Relative hemoglobin concentration in supernatants was monitored by measuring the absorbance at 540 nm. The 100% homolysis was taken from samples in which 1% of Triton X-100 was added to disrupt the membrane. Error bars represent standard deviations from 4 replicates for each condition.

The effectiveness of $D_2S$ in the bacterial killing assays, with complete killing demonstrated at 5 μM, was comparable to ceragenin CSA-13 and cathelicidin LL37 and prompted an investigation into eukaryotic membrane immobilization (Chin et al., 2007, Antimicrob Agents Chemother, 51:1268-1273). Human red blood cells (RBCs) were used to determine toxicity based on the extent of hemoglobin release following exposure to the cationic lipids and the results (FIG. 6c) demonstrate an identical trend to the bacterial killing assay. According to previous observations, membrane asymmetry and the absence of anionic lipids in the outer leaflet of eukaryotic cells account for lower lytic activities of antibacterial peptides compared to bacteria (Bucki and Janmey, 2006, Antimicrob Agents Chemother, 50:2932-2940). The amount of hemoglobin released increased with $D_2S$ concentration in the lipid mixtures with ~100% lysis measured at 500 µM for 100 mol % $D_2S$, a concentration 100 times greater than needed for complete killing of bacteria, indicating a high therapeutic index and possible application of this component as a bactericidal agent (Bucki et al., 2007, J Antimicrob Chemother, 60:535-545). In the present work it has been demonstrated that the ability of $D_2S$ to both bind and inactivate bacterial LPS showing that $D_2S$ can not as a scavenger of LPS preventing binding its target eukaryotic pattern recognition receptors (TRLs) potentially interfering with the inflammatory signaling pathway. In order to assess the ability of $D_2S$ as an inhibitor of bacterial-mediated inflammation, a quantitative measurement of IL-8 released from human neutrophils after incubation with bacterial LPS was performed (FIG. 7a). LPS treated neutrophils were used as a positive control and showed significant increases in IL-8 at 12 hours (15-fold increase) and 24 hours (6-fold increase). Neutrophils treated only with $D_2S$ (5 µM) exhibited a relatively small increase in baseline IL-8 levels compared to the negative controls. An 85% reduction in IL-8 was observed for neutrophils treated with LPS in the presence of $D_2S$ at 12 hours and a 65% reduction was measured at 24 hours compared to the positive controls demonstrating the ability of $D_2S$ to effectively prevent LPS from upregulating IL-8 expression in human neutrophils, which are a primary source of production of proinflammatory cytokines (including IL-8 and TNF-a) (Bucki et al., J Antimicrob Chemother, 60:535-545). Although not wishing to be bound by any particular theory, suppression of bacterial-mediated inflammation may be due to the interaction of $D_2S$ with LPS. However, since this lipid has a base glucocorticoid structure it may be expected that pharmacological activity is providing additional anti-inflammatory activity through cortisol receptor activation, (Price et al., 2005, Mol Ther, 12:502-509), as is suggested by the complete inactivation of a highly inflammatory LPS concentration by $D_2S$. It is important to note that the combined activity of mixtures of DS and $D_2S$ in gene delivery and the demonstrated potential of $D_2S$ to bind and inactivate LPS represents an important connection in light of the recent findings indicating that inflammatory cytokines can directly inhibit gene transfer (Baatz et al., 2001, Biochim Biophys Acta, 1535: 100-109; Bastonero et al., 2005, J Gene Med, 7:1439-1449). Binding of bacterial wall membrane bound LPS to TRL4 initiates signal transmission through the adapter protein myeloid differentiation factor 88 (MyD88), ultimately resulting in upregulation of NFKB controlled transcription of cytokines and chemokines (Schnare et al., 2006, Int Arch Allergy Immunol, 139:75-85). Since activation of NF-KB is also responsible for increased levels of IL-4 and TNF-a, bacterial activation of TRLs could lead to the inhibition of gene transfer, which is particularly relevant in disease targets with known bacterial colonization (i.e. cystic fibrosis). Therefore, prevention of bacterial induced inflammation and cytokine production may further Improve the efficiency of gene transfer.

The results described herein show that liposomes comprised of both DS and $D_2S$ can exhibit improved transfection activity in vitro and in vivo. Several studies have reported optimal activities upon mixing lipids with different hydrophobic domains (Wang and MacDonald, 2007, Mol Pharm, 4:615-623; Wang et al., 2006, Biophys J, 91:3692-3706). Thus, results described herein support the principle that optimal liposomal properties can be obtained from mixing two distinct lipids, instead of progressively engineering new lipids by altering chemical structure. Antimicrobial activity of $D_2S$ against both gram-positive and gram-negative bacteria represents an important area of focus for this molecule due to the large relative difference in effective concentrations between the bacterial and eukaryotic membrane disruption which indicates a favorable therapeutic index. The ability of $D_2S$ to bind and inactivate LPS, effectively suppressing of bacterial-mediated inflammation, may prove to have therapeutic potential in certain diseases targeted by gene therapy and characterized by persistent infection especially considering the evidence that inflammatory cytokines can inhibit of gene transfer.

Example 5

Release from Neutrophils

Experiments were conducted assessing IL-8 release from neutrophils. $D_2S$ significantly prevented release of IL-8 from neutrophils in the presence of LPS (FIG. 7a). IL-8 release from human neutrophils ($3\times10^6$ cells/ml) suspended in RPMI 1640 buffer containing 2% human albumin was measured after activation with LPS (0.1 gg/ml, Sigma) at 12 and 24 hours measured using a sandwich ELISA, according to the manufacturer's instructions (30 pg/ml detection limit, Thermo Fisher Scientific, Rockford, Ill.). Cell-free neutrophil supernatants were collected by centrifugation at 5000×g for 5 min and stored at −80° C. until cytokine determination. Error bars represent standard deviations from 2 replicates for each condition. Transfection of C57Bl/6 mice using β-gal transgene after 24 hours normalized to total protein (solid circles) with group means shown as horizontal bars. (FIG. 7b) Increases in total expression over positive control of DC-Chol:DOPE were observed for both the 60/40 mol % DS/$D_2S$ and $D_2S$ groups. Transgene expression in lung homogenate measured with a chemiluminescent assay for each condition (n=3). Cationic lipids and liposomes (1:1 mole ratio with DOPE) were mixed with plasmid DNA (50 µg/dose) in equal volume at room temperature for 15 minutes prior to instillation. C57Bl/6 mice (6 to 8 weeks of age) were anesthetized by an intraperitoneal (IP) injection of a 3:2 mixture of xylazil: ketamine. For dosing, mice were suspended from their dorsal incisors (hind quarters supported) and a dose of 50 µg DNA with cationic liposome (CR=0.5) was delivered as a 51 µl bolus (delivered as three 17 µl aliquots) into the nostrils. All animal experiments were reviewed and approved by the University of Pennsylvania Institutional Animal Care and Use Committee. For β-gal transgene expression evaluation, lungs were harvested and inflated with a 1:1 mixture of PBS and OCT embedding compound. One lobe was placed in 2 ml of Lysis Buffer (Roche, Indianapolis, Ind.) and placed on ice. Directly after all samples were collected, each sample was homogenized for approximately 10 seconds. The instrument was washed between each sample using 70% ethanol and PBS. Samples were then immediately centrifuged at 3000 rpm (Sorvall; Thermo Scientific, Waltham, Mass.) for 10 min. The supernatant was removed and stored at −80° C. prior to analysis of transgene expression. To quantitatively measure β-gal gene expression a Galacto-Light Plus System (Applied Biosystems, Foster City, Calif.) assay was used on lung homogenates according to the manufacturer's instructions. All values were normalized for total protein content in the sample using the BCA protein assay (Pierce Biotechnology, Inc., Rockford, Ill.) prior to measuring β-gal gene expression. (FIG. 7c) (i) Bioluminescence from *P. aeruginosa* Xen5 at 1×10^6 CFU in BALB/c mice (ii) Bioluminescence following injection of 50 μg $D_2S$ into the right-half of the lung. Both images taken with 5 min exposure. A single colony of kanamycin-resistant *Pseudomonas aeruginosa* Xen5 (Caliper Life Sciences) was selected from a LB plate and grown to mid-log phase (optical density at X=600 of ~0.3) in 2 ml of soy broth (Becton-Dickinson, Cockeysville, Md.). One milliliter of the bacterial suspension was centrifuged at 5000 rpm for 5 minutes at RT, and the bacterial pellet was resuspended in PBS. For in vivo study, BALB/c mice were anesthetized by an intraperitoneal injection of a 3:2 mixture of xylazil:ketamine and suspended from their dorsal incisors (hind quarters supported) for dosing. Bacteria were delivered as a 34111 bolus (delivered as two 17 μl aliquots) into the nostrils. After 5 hours, animals were euthanized prior to by direct injection of D2S (50 μg) in water. All animal experiments were reviewed and approved by the University of Pennsylvania Institutional Animal Care and Use Committee.

Example 6

Average Effective Diameter and Zeta Potential

Figure 8:
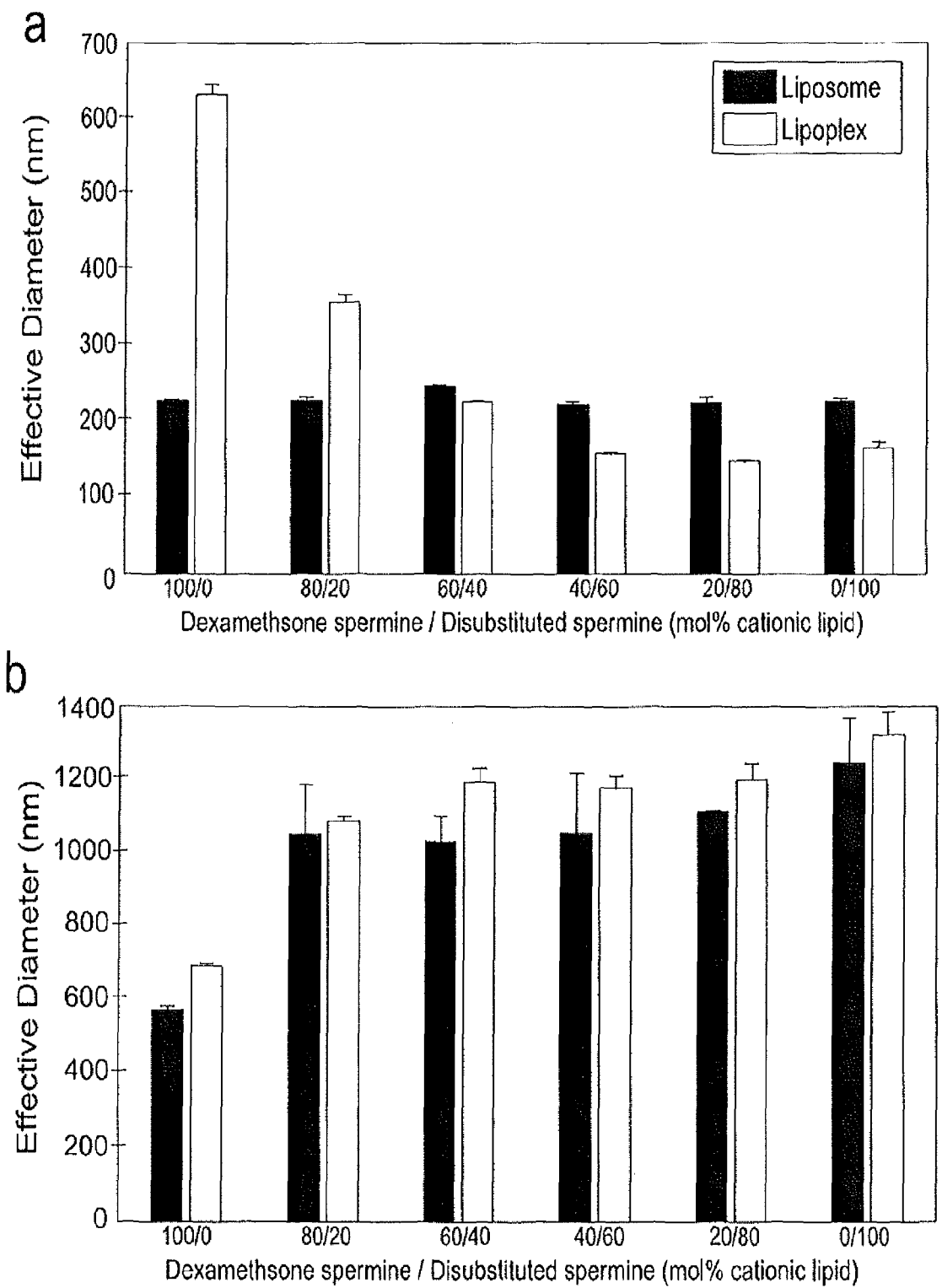
FIG. 8, comprising
Figure 8:
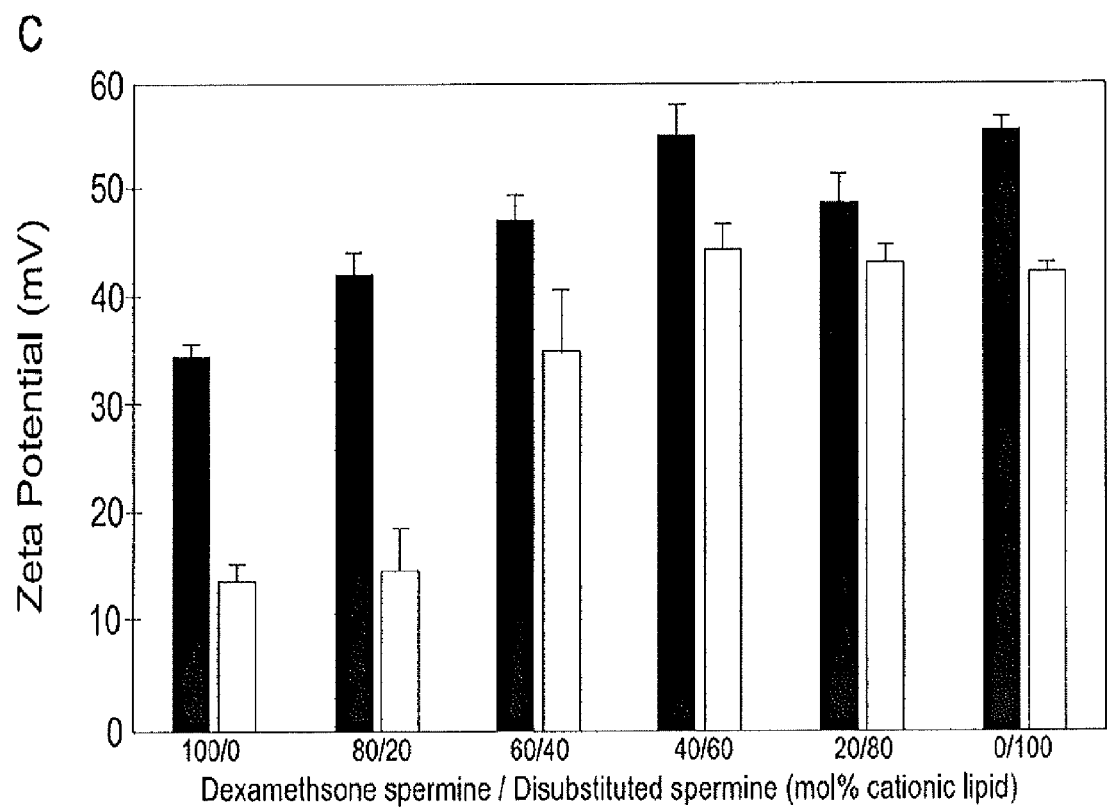

Experiments were conducted assessing the average effective diameter of mixtures of DS and $D_2S$ in water (FIG. 8a) and Optimem (FIG. 8b) from dynamic light scattering. Average zeta potential of mixtures of DS and $D_2S$ in water were also assessed (FIG. 8c). The mean effective diameter for these liposomes in water was nearly constant across the entire series and addition of plasmid DNA resulted in an increase in particle size for all compositions. Particle size in reduced-serum medium is shown in FIG. 5b and demonstrated a transition to relatively larger particles for mixtures containing 20-60 mol % $D_2S$, which correlated directly with the observed peaks in transfection activity in both cell types tested under the same solution conditions. The polydispersity indices of the particle sizes did not change significantly data not shown) indicating uniform size distributions for all measurements. The zeta potential was positive for all conditions as expected since all of the measurements were carried out in excess cationic lipid and a transition to higher zeta potential was noted with the addition of 20-60 mol % $D_2S$. The shift to higher zeta potential correlated with the formation of larger particles and with the peaks in transfection activity in both cell types. Liposomes were formed by adding the cationic lipids in a 1:1 molar ratio to lipid films of 1,2 dioleoylphosphatidylethanolamine (DOPE, Avanti Polar Lipids, Alabaster, Ala.), in either sterile water or reduced serum medium (Optimem, Gibco, Grand Island, N.Y.) to achieve the various charge ratios tested and were probe sonicated for 30 seconds prior to use. Lipoplexes were formed by diluting plasmid DNA in Optimem to achieve a concentration yielding the desired charge ratio upon equal volume mixing with the cationic/DOPE lipid mixture. Lipoplexes were formed 15 minutes prior to use in all experiments. Particle sizes were determined by dynamic light scattering with a Brookhaven Instruments Corporation (Holtsville, N.Y.) ZetaPlus with particle sizing option equivalent to the Brookhaven 90Plus. The measured autocorrelation function (90Plus) is analyzed using a cumulant analysis, the first cumulant yielding an effective diameter, a type of average hydrodynamic diameter. Monodisperse polystyrene microsphere size standards (Polysciences, Warrington, Pa.) were used to validate the DLS instrument. Zeta potential was calculated from the electrophoretic mobility using the ZetaPlus and the Smoluchowski equation. The Doppler shifted frequency spectrum at 15 degrees scattering angle and 25° C. yielded an average Doppler shift that was measured five times and averaged to determine an electrophoretic velocity. The mobility was calculated by dividing the velocity by the electric field strength. Error bars represent standard error from two replicates of 1-minute runs for each condition for dynamic light scattering measurements and 5 replicates of each condition for zeta potential measurements. Open bars indicate liposomes and solid bars indicate lipoplexes.

Example 7

Combined Antibacterial and Anti-Inflammatory Activity in a Cationic Disubstituted Dexamethasone Spermine Conjugate (D2S)

The rising number of antibiotic resistant bacterial strains represents an emerging health problem that has motivated efforts to develop new antibacterial agents. Endogenous cationic antibacterial peptides (CAPs) that are produced in tissues exposed to external environment are one model for design of novel antibacterial compounds. Here, data is described demonstrated that disubstituted dexamethasone-spermine (D2S), a cationic corticosteroid derivative initially identified as a byproduct of synthesis of dexamethasone-spermine for the purpose of improving cellular gene delivery, functions as an antibacterial peptide-mimicking molecule. As described herein, this moiety exhibits bacteria killing activity against clinical isolates of *Staphylococcus aureus*, *Pseudomonas aeruginosa* present in CF sputa, and *Pseudomonas aeruginosa* biofilm. Although its activity is compromised in the presence of plasma, D2S antibacterial activity is maintained in ascites, cerebrospinal fluid, saliva and bronchoalveolar lavage fluid. D2S also prevents IL-6 and IL-8 release from LPS- or LTA-treated neutrophils, suggesting that this molecule might also prevent systemic inflammation caused by bacterial wall products. D2S-mediated translocation of GFP-GR in BAECs indicates that some of its anti-inflammatory activities involve engagement of glucocorticoid receptors. The combined antibacterial and anti-inflammatory activity of D2S suggest its potential as an alternative to natural CAPs in the prevention and treatment of some bacterial infection.

The Materials and Methods used in the present example are now described.

Materials

Tryptic Soy Broth (TSB), Mueller Hinton Agar (MHA) and *Pseudomonas* Isolation Agar were purchased from DIFCO (Sparks, Md.). Brain Heart Infusion Agar (BHI) was from Emapol (Gdansk, Poland) Mannitol Salt Agar (MSA), ID 32 STAPH kit to identified staphylococcal isolates were from bioMerieux, (La Balme Les Grottos, France), E-test to determine susceptibility to methicillin were obtained from AB Biodisk (Solna, Sweden). Beta-Lactamase (cefinase) test was from Becton Dickinson (San Jose, Calif., USA). LPS (*Escherichia coli*, serotype 026:B6) and dexamethasone was purchased from Sigma (St Louis, Mo.), *P. aeruginosa* Xen 5 (a mucoid clinical strain isolated from human septicemia) that was engineered through conjugation and transposition of a plasmid carrying transposon Tn5 luxCDABE, was purchased from Caliper Life Science Inc. (CA, USA). LL-37 and HB-71 peptides were purchased from Bachem (King of Prussia, Pa.). Human IL-6 and IL-8 Elisa kits were obtained from Thermo Fisher Scientific Inc, (Rockwood, Tenn.). Purified LTA (S. aureus) was a kind gift. Solution of human albumin was from Baxter Healthcare Corporation (Glendale, Calif.). DS, D2S and CSA-13 were synthesized as described previously (Ding et al., 2002, J Med Chem 45:663-9). CF sputum samples were collected by spontaneous expectoration from patients attending the University of Pennsylvania Health System Adult Cystic Fibrosis Center at Presbyterian Hospital (PA, USA; IRB-803255).

Antimicrobial Activity

Mannitol salt agar was used to isolate bacteria from clinical specimens. Most Staphylococcus aureus (S. aureus) strains were from puss (infected surgical wounds, diabetic foot or furunculus). S. aureus identification was performed with an ID 32 STAPH kit followed by reading of results using the ATB system bioMerieux, (La Balme Les Grottes, France) according to the manufacturer's instructions. The presence of beta-lactamase and susceptibility to methicillin and vancomycin were determined using cefinase and E-test respectively. For these assays aerobic bacteria growth was conducted in BHI according to provider recommendations. S. aureus susceptibility to macrolides, lincosamides and streptogramins B was evaluated using diffusion methods on MHA with bacterial inoculum at density 0.5 (McFarland scale) (2009, Performance Standards for Antimicrobial Susceptibility Testing; Nineteenth Informational Supplement, Clinical and Laboratory Standarts Institute 29:M-100-S19; Fiebelkorn et al, 2003, J Clin Microbiol 41:4740-4744; Leclercq, 2002, Clin Infect Dis 34:482-492). D2S minimum inhibitory concentration (MIC) and minimum bactericidal concentration (MBC) against different strains of Staphylococcus aureus ($8\times10^5$ cfu/ml) were determined using Muller-Hinton broth and MHA respectively. The bactericidal activities of D28, HB-71 and LL-37 against Pseudomonas aeruginosa (P. aeruginosa) in sputum samples collected from cystic fibrosis (CF) patients with chronic lung infection were measured as previously described (Bucki et al., 2004, Antimicrob Agents Chemother 48:1526-1533). The CF sputa were diluted 10× and 100 IA samples were treated with antibacterial agents (10-200 µM). After a one-hour incubation at 37° C., the suspensions were placed on ice and diluted 10- to 1000-fold. 10 µl aliquots of each dilution were spotted on Pseudomonas isolation agar plates for overnight culture at 37° C. The number of colonies at each dilution was counted the following morning. The colony forming units (CFU/ml) of the individual samples were determined from the dilution factor and were used to calculate the % of bacteria outgrowth.

Biofilm Assay

Starting from an overnight culture of Pseudomonas aeruginosa Xen 5, growth in TRB to late stationary phase, a dilution containing ~$10^8$ cfu/ml was made. For each experiment, bacteria suspensions were placed in 24 well polystyrene plates and a biofilm was allowed to form for 24 hours. Bacteria adherent to the plate were considered a biofilm and cells not adherent to the surface of the plate were considered planktonic and were washed out before D2S addition to individual wells. Biofilm density after D2S treatment was evaluated using Crystal Violet (CV) staining (0.1%) as described previously (Peeters, et al., 2008, J Microbial Methods 72:157-165). The mutagen plasmid (Xen5) gives the P. aeruginosa bacteria a measurable chemiluminescence, which was also quantified using a Fuji Film LAS-300 system before and after D2S treatment as a measure of biofilm viability. Chemiluminescence (densitometry analysis) Was performed using Image Gauge (version 4.22) software (Fuji Photo Film Co, USA).

Evaluation of D2S Antibacterial Activity in Different Body Fluids

Natural CAPs as a part of host defense system can kill bacteria on mucosal or skin surfaces, but their antibacterial activity is inhibited in circulation due to interaction with blood lipoproteins. Accordingly, ApoA-1 was found to specifically interact and inhibit bactericidal ability of cathelicidin LL-37 (Wang, et al., 1998, J Biol Chem 273:33115-33118). Many other factors, present at infection sites such as mucins, negatively charged DNA and F-actin can compromise CAPs bactericidal activity as well (Bucki et al., 2007, Eur Respir J 29:624-632; Herasimenka et al., 2005, Peptides 26:1127-1132; Weiner et al, 2003, Am J Respir Cell Mol Biol 28:738-745). To assess D2S potential to kill bacteria in different environments, changes of P. aeruginosa Xen5 luminescence (~$10^8$ CFU/ml) growth in PBS or PBS mixed with 50% of plasma, ascites, cerebrospinal-fluid, saliva and BAL were evaluated at different times points, up to six hours after D2S addition (10 and 30 µM).

Determination of IL-6 and IL-8 Concentration

Neutrophils were isolated from human blood using the endotoxin-free Lympholyte-poly kit (Cedarlane, Ontario, Canada). At the end of the isolation process, neutrophils were suspended (~$7\times10^6$ cells/ml) in RPMI buffer containing 2% human albumin and activated with LPS from Escherichia coli (50 ng/ml) or LTA from Staphylococcus aureus (10 µg/ml). When required D2S was added to neutrophil samples ~1 minute before LPS or LTA addition. Cell-free neutrophil supernatants were collected 24 hours after addition of bacterial wall products by centrifugation (5000×g, 5 minutes) and stored at −80° C. until cytokine determination. IL-6 and IL-8 were measured using a sandwich enzyme-linked immunosorbent assay (ELISA), according to the manufacturer's instructions. The detection limit was 30 pg/ml.

GFP-GR Translocation Study

BAECs were seeded at $1\times10^5$/ml in 24 well plates and allowed to spread overnight. Cells were transfected with GFP-GR chimeric protein by adding 450 ng of DNA complexed with 2 ul of lipofectamine in a 200 ul volume of Optimem media growth to each well of a 24 well plate for ~1.5 hour. The DNA-lipofectamine complex was then removed and cells placed in DMEM supplemented with 0.5% calf serum. This reduced level of calf serum was used to prevent non-specific translocation of GFP-GR receptor in response to hormones in the serum. After 24 hours, GFP-GR expression was observed in ~70% of cells. The cells were then treated with dexamethasone, DS, D2S, CSA-13 and LL-37 (0.01-1 µM) for 1 hour and imaged. Analysis of GFP-GR translocation was conducted by counting the number of cells in each field of view, which had GFP-GR nuclear localization compared to total number of cells. ~40 cells were analyzed per condition.

The Results of the present example are now described.

Figure 10:
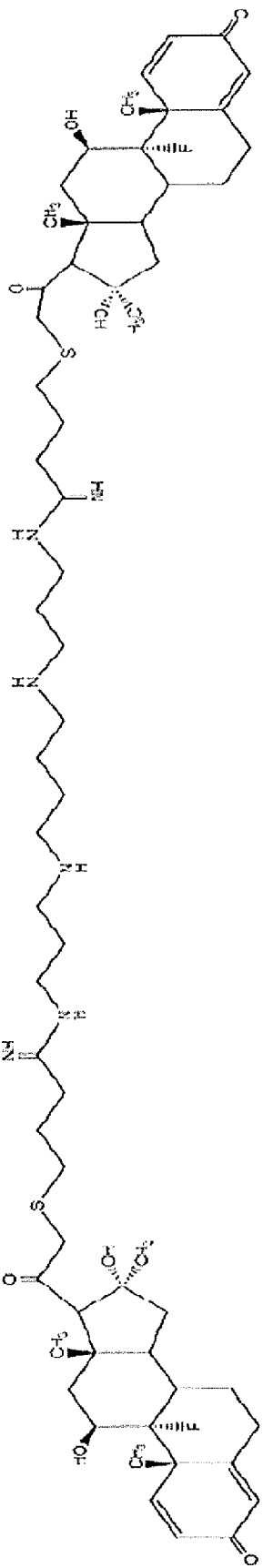
FIG. 10 is a schematic illustration of the structure of LL37, HB71 peptides, and $D_2S$ molecule. For amino acids the one letter code is used.
Figure 11:
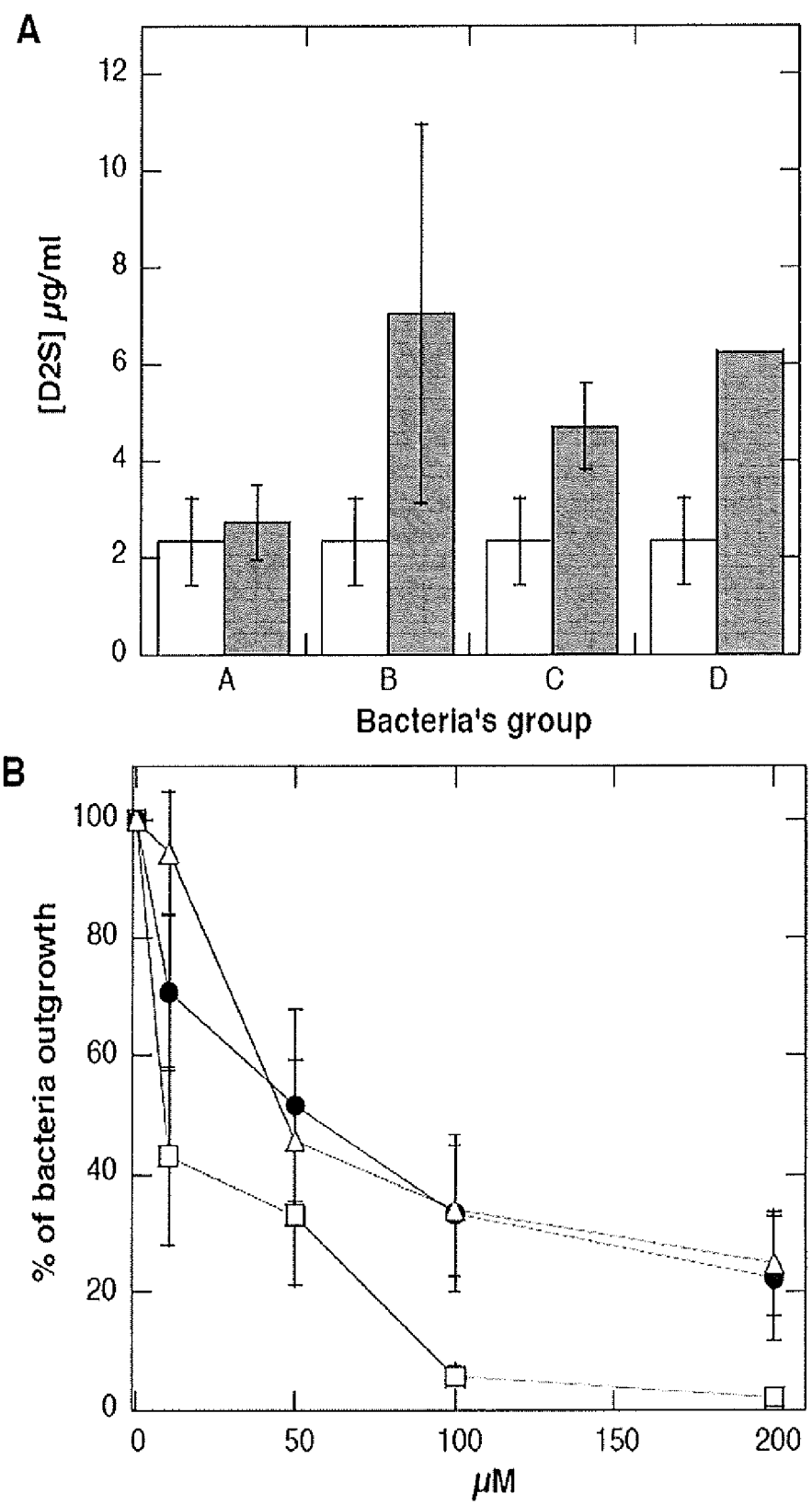
FIG. 11 depicts the results of an example experiment assessing the susceptibility of clinical isolates of *S. aureus*. Panel A. Average minimum inhibitory concentration (white column) and minimum bactericidal concentration (dark column) of D2S against 16 different clinical isolates of *S. aureus*.

D2S Bactericidal Activity Against Clinical Strains of S. aureus and P. aeruginosa Susceptibility testing of the clinical isolates of S. aureus demonstrate that the D28 (FIG. 10) MIC and MBC values range between 1.7-3.6 and 1.7-13.8 pg/ml respectively (FIG. 11A). The observed concentrations that effectively eradicated each of 16 tested clinical strains of *S. aureus* bacteria were similar to those observed for CSA-13 (data not shown) as well as to previously reported CSA-13 values, when its activity was evaluated against clinical isolates of vancomycin-intermediate *S. aureus* (VISA), heterogeneous vancomycin-intermediate *S. aureus* (hVISA), and vancomycin-resistant *S. aureus* (VRSA) (Chin et al., 2007, Antimicrob Agents Chemother 51:1268-1273). Differences in D2S MIC values obtained for four *S. aureus* groups, that were defined based on bacteria susceptibility to methicillin, streptogramins B and presence of beta-lactamase (A, B, C and D; FIG. 11A), were not observed. In the other set of experiments, the antibacterial activity of D2S against clinical strains of *P. aeruginosa* was compared with the antibacterial activity of the naturally occurring antibacterial agent LL-37 peptide and a synthetic HB-71 peptide. This comparison, performed in diluted CF sputum samples, reveals lower bacteria outgrowth after D2S addition than after LL-37 or HB-71 addition (FIG. 11B). The synthetic HB-71 peptide which was selected from 150 antibacterial agents based on a screen against multidrug-resistant clinical isolates of *P. aeruginosa* (Zhang et al., 2005, Antimicrob Agents Chemother 49:2921-2927) was also less effective than CSA-13 (data not shown) suggesting that the strategy to design new antibacterial molecules as antibacterial peptide mimics has more potential then strategies focusing on new cationic peptide sequences.

D2S Activity Against Bacteria Embedded in

Pulmonary infections caused by biofilm-forming *P. aeruginosa* are major risk factors for high morbidity and mortality in patients with cystic fibrosis. In a biofilm state, bacteria are highly resistant to antibiotics and the host immune system. FIG. 12 shows D2S activity in pre-formed *P. aeruginosa* Xen 5 biofilm environment, evaluated using quantification of biofilm mass with CV staining and luminescence measurement indicative of bacteria viability. Because cells (both living and dead), as well as matrix are indistinguishably stained by CV (Pitts et ah, 2003, J Microbial Methods 54:269-276), a decrease in CV staining over time after D2S addition indicates mostly a decrease of biofilm formation. However, D2S treatment may also cause the disruption of pre-formed biofilm. With D2S concentration above 25 µM, the biofilm mass decreased almost 50%, which is above the estimated biofilm growth. The observed decrease in luminescence of *P. aeruginosa* biofilm after D2S treatment indicates a strong ability of these molecules to reach and affect bacterial cells residing in the complex structure of a biofilm mass.

D2S Activity in Different Body Fluids

Bacterial infection takes place in various areas of the body which may affect the antibacterial activity depending on the local environment. To assess the potential of D2S to kill bacteria in different body compartments, the luminescence of *P. aeruginosa* Xen 5 bacteria in PBS suspensions containing 50% of different body fluids including plasma, ascites, cerebrospinal fluid, saliva and BAL was evaluated. Human body fluid specimen collection was performed in accordance with an approved protocol by the Medical University of Bialystok Ethics Committee for Research on Humans and Animals and written consent was obtained from all subjects. In this set of experiments, the ability of D2S to decrease *P. aeruginosa* Xen 5 luminescence was used as a measure of antibacterial activity. An increase of bacteria luminescence (2-15 times) that was observed six hours after bacteria growing in presence of different body fluid, compared to *P. aeruginosa* Xen 5 luminescence in PBS, indicates differences in bacteria growth that likely reflects availability of nutrition and presence of host immune defense molecules (FIG. 13). Under 10 µM D2S treatment, a decrease of bacterial luminescence was observed in all evaluated body fluids except for blood plasma. With an increase of D2S concentration from 10 to 30 µM, luminescence decreased significantly for blood plasma as well as the other body fluids. More precisely, the luminescence decrease in plasma was 26% while in presence of other body fluids such as ascites, cerebrospinal fluid, saliva and BAL reached 91, 88, 96 and 97% respectively.

D2S Prevents LPS and LTA—Induced Release of Interleukins from Human Neutrophils

Interleukin (IL) release, in response to bacteria products during infection, represents an important step towards development of systemic inflammation. Therefore, developing an anti-LPS/LTA molecule would confer an efficient strategy for preventing negative effects of bacteria derived molecules released at infection sites. In human neutrophils, bacterial wall products such as LPS and LTA govern IL production via TLR/NF-kB pathways, which trigger the transcription of pro-inflammatory cytokine genes. Accordingly, as shown in FIG. 14, total amount of IL-6 and IL-8 detected in neutrophil supernatant 24 hours after their activation was significantly higher compared to the amount detected in non-activated samples, D2S treatment (10-20 µM) results in a significant and concentration dependent decrease in IL-6 and IL-8 release from neutrophils (FIG. 14). These data suggest that D2S tightly binds to LPS and LTA and this binding results in attenuation of bacterial wall products' ability to reach and activate TLR.

D2S Glucocorticoid Activity

Nuclear localization of GR is one test of glucocorticoid activity that was previously used to study DS pharmacological effects (Gruneich et al, 2004, Gene Ther 11:668-674). As shown on FIG. 15A, efficient transfection of BAECs results in a fluorescent signal that can be detected and analyzed with microscopy. A 60-minute treatment of BAECs expressing GFP-GR, protein with dexamethasone, DS or D2S caused nuclear localization of GFP-GR at doses from 0.01-1 µM. However, CFP-GR translocation was not observed with CSA-13 treatment and LL-37 (data not shown) at similar tested concentrations (FIG. 15B). This finding indicates that D2S has strong glucocorticoidal activity, which should enlarge the spectrum of its anti-inflammatory action.

Antibacterial Activity of LL-37 Peptide and D2S Against Pathogens Associated with Oral Infections The antibacterial activity for LL-37 peptide and D2S was measured following the methods discussed elsewhere herein. Briefly, susceptibility testing of the pathogens associated with oral infections was conducted. MIC and MBC values for D2S were compared with the values for the naturally occurring antibacterial agent LL-37 peptide as well as AMC (amoxicillin/clavulonic acid). See FIG. 16. The observed concentrations that effectively eradicated each of tested pathogens associated with oral infection were general lower using D2S compared to LL-37 peptide. The results presented herein demonstrate that D2S is a novel antibacterial molecule for treating oral infections.

The antibacterial activity for the LL-37 peptide and D2S was also evaluated against bacterial isolated from dental plaque. MIC and MBC values for D2S were compared with the values for the naturally occurring antibacterial agent LL-37 peptide. See FIG. 17. The results presented herein demonstrate that D2S is a novel antibacterial molecule for treating oral infections.

D2S Activity in Different Body Fluids

Bacterial infection takes place in various areas of the body which may affect the antibacterial activity depending on the local environment. To assess the potential of D2S to kill bacteria in different body compartments, the luminescence of *P. aeruginosa* Xen 5 bacteria in PBS suspensions containing 50% of different body fluids including plasma, cerebrospinal fluid, saliva, abdominal fluid, BAL, and urine was evaluated as discussed elsewhere herein. In this set of experiments, the ability of D2S to decrease *P. aeruginosa* Xen luminescence was used as a measurement of antibacterial activity. See FIG. 18.

The ability of D2S to kill bacteria in different body compartments was also evaluated with respect to *S. aureus* Xen29 bacteria. The luminescence of *S. aureus* Xen29 bacteria in PBS suspensions containing 50% of different body fluids including plasma, cerebrospinal fluid, saliva, abdominal fluid, BAL, and urine was evaluated as discussed elsewhere herein. In this set of experiments, the ability of D2S to decrease *S. aureus* Xen29 luminescence was used as a measure of antibacterial activity. See FIG. 19.

The results presented herein demonstrate that D2S is able to kill different types of bacteria in different body compartments. In summary, the results presented heroin demonstrate that D2S can exhibit antimicrobial activity in biological environments.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true split and scope of the invention. The appended claims are intended to be construed to include all such embodiments and equivalent variations.

What is claimed is:

1. A method of treating an infection in a subject in need thereof, the method comprising administering to the subject a conjugated dexamethasone-spermine compound, wherein the compound is the only active antimicrobial agent administered to the subject, wherein in the compound the spermine is conjugated to the C-21 position of the dexamethasone,
   wherein administration of the compound to the subject treats the infection in the subject; and
   wherein the infection is caused by a bacterium selected from the group consisting of *Bacillus subtilis, Enterococcus faecalis, Escherichia coli, Fusobacterium nucleatum, Helicobacter pylori, Lactobacillus casel, Moraxella catarrhalis, Peptostreptococcus anaerobius, Porphyromonas gingivalis, Pseudomonas aeruginosa, Staphylococcus aureus, Streptococcus mutans, Streptococcus pneumoniae, Streptococcus pyogenes, Streptococcus salivarius, Streptococcus sanguinis,* and *Tannerella forsythensis.*

2. The method of claim 1, wherein the compound comprises a first dexamethasone conjugated through the C-21 position to a first primary amine on the spermine and a second dexamethasone conjugated through the C-21 position to a second primary amine on the spermine.

3. The method of claim 1, wherein the subject is a human.

4. A method of treating an infection in a subject in need thereof, the method comprising administering to the subject a therapeutically effective amount of a conjugated steroid-polyamine compound, wherein the compound is the only active antimicrobial agent administered to the subject, wherein the steroid is dexamethasone and the polyamine is spermine;
   wherein the compound is prepared by a method comprising the steps of: mixing a steroid, a conjugating reagent, and a polyamine, wherein the conjugating reagent conju-

---

SEQUENCE LISTING

```
<160> NUMBER OF SEQ ID NOS: 2

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 18
<212> TYPE: PRT
<213> ORGANISM: Homo sapiens

<400> SEQUENCE: 2

Phe Ala Lys Lys Leu Ala Lys Lys Leu Lys Lys Leu Ala Lys Lys Leu
1               5                   10                  15

Ala Lys
``` gates the polyamine through the C-21 position of the steroid to generate the compound, and purifying the compound;

wherein administration of the compound to the subject treats the infection in the subject; and wherein the infection is caused by a bacterium selected from the group consisting of *Bacillus subtilis, Enterococcus faecalis, Escherichia coli, Fusobacterium nucleatum, Helicobacter pylori, Lactobacillus casel, Moraxella catarrhalis, Peptostreptococcus anaerobius, Porphyromonas gingivalis, Pseudomonas aeruginosa, Staphylococcus aureus, Streptococcus mutans, Streptococcus pneumoniae, Streptococcus pyogenes, Streptococcus salivarius, Streptococcus sanguinis*, and *Tannerella forsythensis*.

5. The method of claim 4, wherein the compound comprises is a first dexamethasone conjugated through the C-21 position to a first primary amine on the spermine and a second dexamethasone conjugated through the C-21 position to a second primary amine on the spermine.

6. The method of claim 4, wherein the conjugating reagent is 2-iminothiolane.

7. The method of claim 4, wherein the subject is a human.

* * * * *